(12) United States Patent
Katze et al.

(10) Patent No.: US 6,326,151 B1
(45) Date of Patent: *Dec. 4, 2001

(54) SCREENING METHODS TO IDENTIFY AGENTS THAT SELECTIVELY INHIBIT HEPATITIS C VIRUS REPLICATION

(75) Inventors: Michael G. Katze, Seattle; Michael J. Gale, Monroe, both of WA (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/514,006

(22) Filed: Feb. 25, 2000

Related U.S. Application Data

(63) Continuation of application No. 09/035,619, filed on Mar. 5, 1998, now Pat. No. 6,030,785.
(60) Provisional application No. 60/038,596, filed on Mar. 5, 1997.

(51) Int. Cl.[7] ........................................................ C12Q 1/68
(52) U.S. Cl. ........................ 435/6; 435/375; 435/254.11; 435/254.21
(58) Field of Search .................................. 514/44; 435/6, 435/375, 254.21, 254.11

(56) References Cited

U.S. PATENT DOCUMENTS 6,030,785  2/2000  Katze et al. .

OTHER PUBLICATIONS

Branch, *TIBS*, vol. 23, pp. 45–50, (Feb. 1998).*
Gura, *Science*, vol. 278, pp. 1041–1042, (Nov. 1997).*
Alter, 1995, "Epidemiology of hepatitis C in the West," Semin. Liver Dis. 15(1):5–14.
Barber et al., 1994, "The 58–kilodalton inhibitor of the interferon–induced double–stranded RNA–activated protein kinase is a tetratricopeptide repeat protein with oncogenic properties", Proc. Natl. Acad. Sci. USA 91(10):4278–82.
Beattie et al., 1991, "Vaccina virus–encoded eIF–2α homolog abrogates the antiviral effect of interferon", Virology 183:419–422.
Beattie et al., 1995, "Distinct patterns of IFN sensitivity observed in cells infected with Vaccina K3L⁻ and E3L⁻ mutant viruses", Virology 210:254–263.
Bukh et al., 1995, "Genetic heterogeneity of hepatitis C virus: quasispecies and genotypes", Semin. Liver Dis. 15(1):41–63.
Carroll et al., 1993, "Recombinant vaccina virus K3L gene product prevents activation of double–stranded RNA–dependent, initiation factor 2α–specific protein kinase", J. Biol. Chem. 268:12837–12842.
Craig et al., 1996, "The kinase insert domain of interferon–induced protein kinase PKR is required for activity but not for interaction with the pseudosubstrate K3L", J. Biol. Chem. 271(40):24526–33.
Cuthbert, 1994, "Hepatitis C: progress and problems", Clin. Microbiol. Rev. 7(4):505–32.
Davidson et al., 1995, "Survey of major genotypes and subtypes of hepatitis C virus using RFLP of sequences amplified from the 5' non–coding region", J. Gen. Virol. 76 ( Pt 5):1197–204.
Dever et al., 1993, "Mammalian eukaryotic initiation factor 2α kinases functionally substitute for GCN2 protein kinase in the GCN4 translational control mechanism of yeast", Proc. Natl. Acad. Sci. USA 90:4616–4620.
Di Bisceglie, 1995, "Hepatitis C and hepatocellular carcinoma", Semin. Liver Dis. 15(1):64–9.
Enomoto et al., 1995, "Comparison of full–length sequences in interferon–sensitive and resistant hepatitis C virus 1b. Sensitivity to interferon is conferred by amino acid substitutions in the NS5A region", J. Clin. Invest. 96(1):224–30.
Enomoto et al., 1996, "Mutations in the nonstructural protein 5A gene and response to interferon in patients with chronic hepatitis C virus 1b infection", N. Engl. J. Med. 334(2):77–81.
Fields and Song, 1989, A novel genetic system to detect protein–protein interactions. Nature 340(6230):245–6.
Fried and Hoofnagle, 1995, "Therapy of hepatitis C", Semin. Liver Dis. 15(1):82–91.
Gale Jr. et al., 1996, "Interaction of the interferon–induced PKR protein kinase with inhibitory proteins P58$^{IPK}$ and Vaccina virus K3L is mediated by unique domains: implications for kinase regulation", Mol. Cell. Biol. 16:4172–4181.
Gale et al., 1997, "Evidence that hepatitis C virus resistance to interferon is mediated through repression of the PKR protein kinase by the nonstructural 5A protein", Virology 230(2):217–27.
Germandis et al., 1997, "Is there an interferon sensitivity determining region (ISDR) in the NS5A gene of hepatitis C virus", J. Hepatol. 26:93 (Abstract P/C01/66).

(List continued on next page.)

Primary Examiner—James Ketter
(74) Attorney, Agent, or Firm—Robin M. Silva, Esq.; Flehr Hohbach Test Albritton & Herbert LLP

(57) ABSTRACT

The present invention relates to novel methods for identifying antiviral agents which selectively interfere with viral proteins that override the interferon(IFN)-induced cellular defense mechanisms against viral infection. In particular, the present invention relates to screening assays that identify agents which selectively inhibit the interaction between viral proteins containing an interferon sensitivity determining region (ISDR) and IFN-induced PKR protein kinase. The present invention more particularly relates to screening assays that identify agents which selectively inhibit the interaction between hepatitis C virus (HCV) nonstructural 5A protein (NS5A), which contains an ISDR, and IFN-induced PKR protein kinase. The interaction between the viral ISDR and IFN-induced PKR protein kinase results in the override of IFN-induced cellular defense mechanisms to combat viral infection. Therefore the agents identified using the assays of the invention may have utility as antiviral agents.

22 Claims, 18 Drawing Sheets

OTHER PUBLICATIONS

Figure 1:
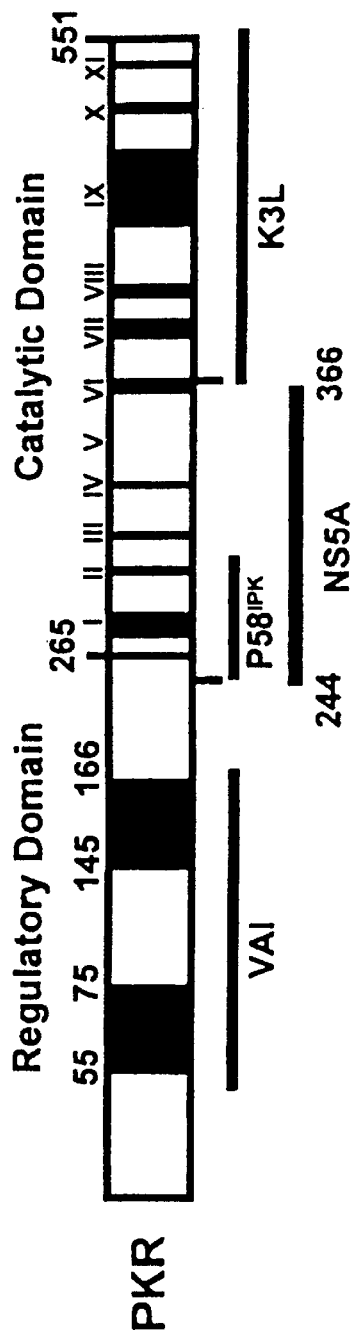

Hoofnagle, 1994, "Therapy of acute and chronic viral hepatitis", Adv. Intern. Med. 39:241–75.

Hu et al., 1990, "Sequence requirements for coiled–coils: analysis with lambda repressor–GCN4 leucine zipper fusions", Science 250(4986):1400–3.

Hu, 1995, "Repressor fusions as a tool to study protein–protein interactions", Structure 3(5):431–3.

Kato et al., 1990, "Molecular cloning of the human hepatitis C virus genome from Japanese patients with non–A, non–B hepatitis", Proc. Natl. Acad. Sci. USA 87(24):9524–8.

Katze et al., 1987, "Adenovirus VAI RNA complexes with the 68,000 $M_r$ protein kinase to regulate its autophosphorylation and activity", EMBO J. 6:689–697.

Katze et al., 1991, "Functional expression and RNA binding analysis of the interferon–induced, double–stranded RNA–activated, 68,000–Mr protein kinase in a cell–free system", Mol. Cell. Biol. 11(11):5497–505.

Kumar et al., 1988, "Studies on the role of the 2'–5'–oligoadenylate synthetase–Rnase L pathway in beta interferon–mediated inhibition of encephalomyocarditis virus replication", J. Virol. 62:3175–3181.

Lee et al., 1994, "The 58,000–dalton cellular inhibitor of the interferon–induced double–stranded RNA–activated protein kinase (PKR) is a member of the tetratricopeptide repeat family of proteins", Mol. Cell. Biol. 14:2331–2342.

Lee et al., 1990, "Purification and partial characterization of a cellular inhibitor of the interferon–induced protein kinase of $M_r$ 68,000 from influenza virus–infected cells", Proc. Natl. Acad. Sci. USA 87:6208–6212.

Mansell and Locarnini, 1995, "Epidemiology of hepatitis C in the East", Semin. Liver Dis. 15(1):15–32.

McMillan et al., 1995, "HIV–1 Tat directly interacts with the interferon–induced, double–stranded RNA–dependent kinase, PKR", Virology 213:413–424.

Meurs et al., 1990, "Molecular cloning and characterization of the human double–stranded RNA–activated protein kinase induced by interferon", Cell 62:379–390.

Okamoto et al., 1992, "Typing hepatitis C virus by polymerase chain reaction with type–specific primers: application to clinical surveys and tracing infectious sources", J. Gen. Virol. 73 ( Pt 3):673–9.

Romano et al., 1995, "Structural requirements for double–stranded RNA binding, dimerization, and activation of the human eIF–2α kinase DAI in *Saccharomyces cerevisiae*", Mol. Cell. Biol. 15:365–378.

Sen and Ransohoff, 1993, "Interferon–induced antiviral actions and their regulation", Adv. Virus Res. 42:57–102.

Sen and Lengye, 1992, "The interferon system", J. Biol. Chem. 267:5017–5020.

Tang et al., 1996, "The 58–kDa cellular inhibitor of the double stranded RNA–dependent protein kinase requires the tetratricopeptide repeat 6 and DnaJ motifs to stimulate protein synthesis in vivo", J. Biol. Chem. 271(45):28660–6.

Tomita and Kuwata, 1981, "Suppressive effects of interferon on cell fusion by Sendai virus", J. Gen. Virol. 55:289–295.

Whitaker–Dowling et al., 1983, "Interferon–mediated inhibition of virus penetration", Proc. Natl. Acad. Sci. USA 80:1083–1086.

Wymann et al., 1996, "Wortmannin inactivates phosphoinositide 3–kinase by covalent modification of Lys–802, a residue involved in the phosphate transfer reaction", Mol. Cell. Biol. 16:1722–1733.

* cited by examiner 2180-2251

2209-2274

1973-2208

2120-2274

1973-2419

1973-2361

FIG.10B

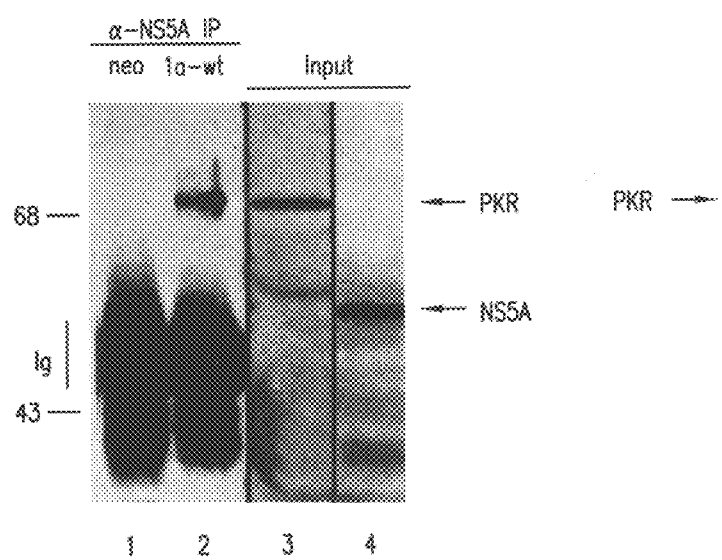
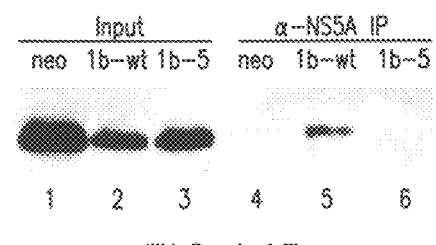
FIG.14A
FIG.14B

SEQUENCE LISTING

<160> NUMBER OF SEQ ID NOS: 25

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 1
ggaattcgag ctcgcccg                                                 18

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 2
gctctagaag cacacgacat cttc                                          24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 3
ccactcgagc ggacagttgg ctgg                                          24

<210> SEQ ID NO 4
<211> LENGTH: 25
<212> TYPE: DNA

```
<213> ORGANISM: Artificial Sequence
<220> FEATURE:
<223> OTHER INFORMATION: Description of Artificial Sequence: primer

<400> SEQUENCE: 4
ccgctcgagt ggtgattctg gtctc                                        25

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 5
gtggtgacgc agcagagagt                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 6
cagcctcacc atcactcagc                                              20

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 7
ccttccatgg gctccggctc gtggctaaag                                   30

<210> SEQ ID NO 8
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 8
atcggatcct taggacattg agcagcagac ga                                32

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 9
gtgactggtg aggcctcaac caagtc                                       26

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 10
taagcttatg ggctccggct cgtggct                                      27
```

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 11
catatgggct ccggctcgtg gcta                                        24

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 12
gaattccctt ccttgaaggc aacatgc                                     27

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 13
ccttccatgg cccacattac agcagagacg                                  30

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 14
caagcttgga tccttaggac attgagc                                     27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 15
gtcgaccgca gacaactggc tagctga                                     27

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 16
atcggatcct tataccacct tattctctga                                  30

<210> SEQ ID NO 17
<211> LENGTH: 30
<212> TYPE: DNA
<213> ORGANISM: Artificial Sequence
<220> FEATURE:

```
<223> OTHER INFORMATION: Description of Artificial Sequence: primer

<400> SEQUENCE: 17
atcggatcct taccacct tattctctga                                    30

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 18
gactccccag atgttgacct catc                                        24

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 19
ttgtctgcgc tttccttgaa ggcagcatgc actggccgtc acgac                 45

<210> SEQ ID NO 20
<211> LENGTH: 40
<212> TYPE: PRT
<213> ORGANISM: Hepatitis C virus

<400> SEQUENCE: 20

Pro Ser Leu Lys Ala Thr Cys Thr Thr His His Asp Ser Pro Asp Ala
 1               5                  10                  15

Asp Leu Ile Glu Ala Asn Leu Leu Trp Arg Gln Glu Met Gly Gly Asn
            20                  25                  30

Ile Thr Arg Val Glu Ser Glu Asn
        35                  40

<210> SEQ ID NO 21
<211> LENGTH: 40
<212> TYPE: PRT
<213> ORGANISM: Hepatitis C virus

<400> SEQUENCE: 21

Pro Ser Leu Lys Ala Thr Cys Thr Ala Asn His Asp Ser Pro Asp Ala
 1               5                  10                  15

Glu Leu Ile Glu Ala Asn Leu Leu Trp Arg Gln Glu Met Gly Gly Asn
            20                  25                  30

Ile Thr Arg Val Glu Ser Glu Asn
        35                  40

<210> SEQ ID NO 22
<211> LENGTH: 40
<212> TYPE: PRT
<213> ORGANISM: Hepatitis C virus

<400> SEQUENCE: 22

Pro Ser Leu Lys Ala Thr Cys Thr Thr Arg His Asp Ser Pro Asp Ala
 1               5                  10                  15

Asp Leu Ile Glu Ala Asn Leu Leu Trp Arg Gln Glu Met Gly Gly Asn
            20                  25                  30

Ile Thr Arg Val Glu Ser Glu Asn
```

-continued

<210> SEQ ID NO 23
<211> LENGTH: 40
<212> TYPE: PRT
<213> ORGANISM: Hepatitis C virus

<400> SEQUENCE: 23

Pro Ser Leu Lys Ala Thr Cys Thr Thr Arg His Asp Ser Pro Asp Val
 1               5                  10                  15

Asp Leu Ile Glu Ala Asn Leu Leu Trp Arg Gln Glu Met Gly Gly Asn
            20                  25                  30

Ile Thr Arg Val Glu Ser Glu Asn
        35                  40

<210> SEQ ID NO 24
<211> LENGTH: 40
<212> TYPE: PRT
<213> ORGANISM: Hepatitis C virus

<400> SEQUENCE: 24

Leu Ser Leu Lys Ala Ala Cys Thr Gly Arg His Asp Ser Pro Asp Ala
 1               5                  10                  15

Asp Leu Ile Glu Ala Asn Leu Leu Trp Arg Gln Glu Met Gly Gly Asn
            20                  25                  30

Ile Thr Arg Val Glu Ser Glu Asn
        35                  40

<210> SEQ ID NO 25
<211> LENGTH: 40
<212> TYPE: PRT
<213> ORGANISM: Hepatitis C virus

<400> SEQUENCE: 25

Leu Ser Leu Lys Ala Ala Cys Thr Gly Arg His Asp Ser Pro Asp Val
 1               5                  10                  15

Asp Leu Ile Glu Ala Asn Leu Leu Trp Arg Gln Glu Met Gly Gly Asn
            20                  25                  30

Ile Thr Arg Val Glu Ser Glu Asn
        35                  40

SCREENING METHODS TO IDENTIFY AGENTS THAT SELECTIVELY INHIBIT HEPATITIS C VIRUS REPLICATION

This is a continuation of application Ser. No. 09/035,619, filed Mar. 5, 1998 now U.S. Pat. No. 6,030,785, which is incorporated by reference herein in its entirety.

This application claims benefit of U.S. provisional application Ser. No. 60/038,596, filed Mar. 5, 1997.

1. INTRODUCTION

The present invention relates to novel methods for identifying antiviral agents which selectively interfere with viral proteins that override the interferon(IFN)-induced cellular defense mechanisms against viral infection. In particular, the present invention relates to screening assays that identify agents which selectively inhibit the interaction between viral proteins containing an interferon sensitivity determining region (ISDR) and IFN-induced PKR protein kinase. The present invention more particularly relates to screening assays that identify agents which selectively inhibit the interaction between hepatitis C virus (HCV) nonstructural 5A protein (NS5A), which contains an ISDR, and IFN-induced PKR protein kinase. The interaction between the viral ISDR and IFN-induced PKR protein kinase results in the override of IFN-induced cellular defense mechanisms to combat viral infection. Therefore the agents identified using the assays of the invention may have utility as antiviral agents.

2. BACKGROUND

2.1 IFN THERAPY FOR TREATMENT OF VIRAL INFECTION

Interferons are extracellular signaling proteins which have many diverse effects, including immune stimulation, tumor inhibition, and cell multiplication reduction. Interferon induces host cell production of many gene products, including the Mx proteins, the 2'-5' oligoadenylate synthetase and RNase L. (reviewed in Sen et al., 1992, J. Biol. Chem. 267:5017–5020; Sen et al., 1993, Adv. Virus. Res. 42:57). In addition, PKR, a cAMP-independent serine/threonine kinase, is one of the greater than 30 INF-induced gene products (Meurs et al., 1990, Cell 62:379–590). These proteins have been shown to have a protective effect against viral infection, thus contributing to the beneficial effects of IFN therapies in treating viral infections.

There are many mechanisms by which IFN-induced gene products provide a protective effect against viral infection. For example, the IFN-induced double-stranded RNA-dependent enzyme, 2'-5' oligoadenylate synthetase activates an RNase that cleaves cellular and viral RNAs, thereby inactivating viral replication, such as picornavirus replication (Kumar et al, 1988, J. Virol. 62:3175–3181). The IFN-induced double-stranded RNA-dependent protein kinase inhibits virus and host cell protein synthesis by phosphorylating and inactivating the α subunit of the translational initiation factor eIF-2α. IFN also has inhibitory viral effects at different stages of the viral life cycle. IFN inhibits uncoating of hepatitis B viral particles, thereby inhibiting viral replication. IFN inhibits the penetration of vesicular stomatitis virus into cells (Whitaker-Dowling et al., 1983, Proc. Natl. Acad. Sci. 80:1083–1086). IFN also inhibits cell fusion caused by viruses, such as Sendai virus (Tomita et al., 1981, J. Gen. Virol. 55:289–295).

To counteract the deleterious effects of IFN-induced cellular defense mechanisms, many eukaryotic viruses have evolved mechanisms to block the activity of IFN-induced proteins. A number of viruses produce RNAs which override the IFN-induced host cell shut off of translation, for example, the adenovirus produced VAI RNA molecule, human immunodeficiency virus (HIV) TAR region, and the Epstein-Barr virus produced EBER-1 RNA molecule (Katz et al., 1987, Embo. J. 6:689–697; McMillan et al., 1995, Virology 213:413–424; Carroll et al., 1993; Beattie et al., 1995, Virology 210:254–263; Beattie et al., 1991, Virology 183:419–422). A number of viruses such as the vaccinia virus K3L protein, which binds to and inhibits IFN-induced PKR protein kinase (Gale Jr. et al., 1996, Mol. Cell. Biol. 16:4172–4181). Influenza virus, recruit cellular factors, such as P58 which binds to and blocks PKR protein kinase (Lee et al., 1990, Proc. Natl. Acad. Sci. 87:6208–6212; Lee et al., 1994, Mol. Cell. Biol. 14:2331–2342).

2.2 HEPATITIS C VIRUS

Hepatitis C virus (HCV) infection is an important clinical problem worldwide. In the United States alone, an estimated four million individuals are chronically infected with HCV. HCV, the major etiologic agent of non-A, non-B hepatitis, is transmitted primarily by transfusion of infected blood and blood products (Cuthbert et al., 1994, Clin. Microbiol. Rev. 7:505–532; Mansell et al., 1995, Semin. Liver Dis. 15:15–32). Prior to the introduction of anti-HCV screening in mid-1990, HCV accounted for 80–90% of posttransfusion hepatitis cases in the United States. Currently, injection drug use is probably the most common risk factor for HCV infection, with approximately 80% of this population seropositive for HCV. A high rate of HCV infection is also seen in individuals with bleeding disorders or chronic renal failure, groups that have frequent exposure to blood and blood products.

Acute infection with HCV results in persistent viral replication and progression to chronic hepatitis in approximately 90% of cases. For many patients, chronic HCV infection results in progressive liver damage and the development of cirrhosis. In patients with an aggressive infection, cirrhosis can develop in as little as two years, although a time span of 10–20 years is more typical. In 30–50% of chronic HCV patients, liver damage may progress to the development of hepatocellular carcinoma. In general, hepatocellular carcinoma is a late occurrence and may take greater than 30 years to develop (Bisceglie et al., 1995, Semin. Liver Dis. 15:64–69). The relative contribution of viral or host factors in determining disease progression is not clear.

HCV is an enveloped virus containing a positive-sense single-stranded RNA genome of approximately 9.5 kb. On the basis of its genome organization and virion properties, HCV has been classified as a separate genus in the family Flaviviridae, a family that also includes pestiviruses and flaviviruses (Alter, 1995, Semin. Liver Dis. 15:5–14). The viral genome consists of a lengthy 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as internal ribosome entry. This mechanism involves the binding of ribosomes to an RNA sequence known as the internal ribosome entry site (IRES). An RNA pseudoknot structure has recently been determined to be an essential structural element of the HCV IRES. Although a reliable tissue culture system permissive for HCV replication has yet to be developed, viral proteins have been identified by a variety of techniques, including the use of recombinant vaccinia virus constructs and transcription/translation systems. The polyprotein precursor is cleaved by both host and viral proteases to yield mature viral structural and nonstructural proteins. Viral structural proteins include a nucleocapsid core protein (C) and two envelope glycoproteins, E1 and E2. HCV also encodes two proteinases, a zinc-dependent metalloproteinase, encoded by the NS2-NS3 region, and a serine proteinase encoded in the NS3 region. These proteinases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown.

Progress in understanding HCV replication and pathogenesis has been severely hampered by the lack of an cell culture system. As a result, effective antiviral strategies against HCV infection have yet to be developed. Treatment with alpha interferon is currently the sole therapy for chronic HCV infection. However, less than 50% of patients have sustained remissions following treatment, with the eradication of HCV (Hoofnagle et al., 1994; Lino et al., 1994, Intervirology 37:87–100). As discussed above, there is a correlation between HCV genotype and response to interferon therapy (Enomoto et al., 1996, N. Engl. J. Med. 334:77–81; Enomoto et al., 1995, J. Clin. Invest. 96:224–230). For example, the response rate in patients infected with HCV-1b is less than 40%. Similar low response rates for patients infected with prototype United States genotype, HCV-1a, have also been reported (Hoofnagle et al., Lino et al, 1994, Intervirology 37:87–100). In contrast, the response rate of patients infected with HCV genotype-2 is nearly 80% (Fried et al., 1995, Semin. Liver Dis. 15:82–91).

The amino acid sequence of a discrete region of the NS5A protein of genotype 1b was found to correlate with sensitivity to interferon (Enomoto et al., 1996, Enomoto et al., 1995). This region, termed the interferon sensitivity determining region (ISDR), spans amino acid residues 237 to 276 of NS5A [amino acids 2209 to 2248 of the polyprotein; numbering based on that of HCV-J, an HCV-1b strain for which the complete genomic sequence has been determined (Enomoto et al., 1995). Interferon-resistant strains (i.e., quasispecies that were present prior to, as well as six months post-interferon therapy) possess the same ISDR sequence as that of the prototype HCV-1b strain (Enomoto et al., 1996). In contrast, an interferon-sensitive strains (HCV quasispecies that were present prior to interferon treatment but absent six months post-therapy) multiple amino acid substitutions are found within the ISDR. In this study, patients infected with HCV isolates containing four to 11 amino acid changes within the ISDR showed a complete response to interferon therapy. In contrast, in patients infected with HCV isolates containing the prototype ISDR sequence (and 87% of those infected with HCV isolates containing one to three amino acid changes within the ISDR) no response to therapy was observed. The mechanism by which the ISDR of HCV-1b influences the response to interferon is not known.

3. SUMMARY OF THE INVENTION

The present invention relates to novel methods for identifying antiviral agents which selectively inactivate viral proteins which override interferon(IFN)-induced cellular defense mechanisms against viral infection. In particular, the present invention relates to screening assays that identify agents which selectively inhibit the interaction between viral proteins expressing an ISDR and IFN-induced PKR protein kinase. The present invention more particularly relates to screening assays that identify agents which selectively inhibit the interaction between HCV nonstructural 5A protein (NS5A), which contains an ISDR, and IFN-induced PKR protein kinase. In one embodiment, the present invention relates to screening assays that identify agents which selectively inhibit viral proteins which prevent the dimerization of PKR. The present invention further relates to screening assays to identify novel exogenous or endogenous agents that induce IFN-expression to a level that results in an override of NS5A inhibition of PKR protein kinase. The interaction between the viral protein containing an ISDR and IFN-induced PKR protein kinase results in the override of IFN-induced cellular defense mechanisms to combat viral infection, therefore the agents identified to interfere with this interaction will have utility as antiviral agents.

The invention is based in part, on the Applicants'discovery that (1) the HCV protein NS5A directly interacts with and inhibits the IFN-induced PKR protein kinase; and (2) the ISDR is required for NS5A to interact and inhibit PKR protein kinase.

The present invention further encompasses the novel agents identified by the screening assays described herein. The invention relates to therapeutic modalities and pharmaceutical compositions for the treatment of viral infections using ISDR containing proteins as the target for intervention. The present invention more particularly relates to therapeutic modalities and pharmaceutical compositions for the treatment of HCV-infection by targeting NS5A and its interaction with IFN-induced PKR protein kinase.

Such drugs should be more effective than currently used drugs because they will have the advantage in that they do not interfere with cellular processes, rather they block viral inhibition of cellular defense mechanisms against viral infection. These drugs will have minimal side effects because they are targeting viral proteins which do not have host homologues so that they will not be injurious to the host cell. Therefore, their minimal side effects allow them to be used at higher dosages.

The present invention also relates to the use of antiviral agents identified by the present invention in combinatorial therapies with other known antiviral agents to inhibit viral replication. The agents identified by the screening assays of the present invention also have utility in reducing the virus's resistance to IFN, and thus would be useful to increase the efficacy of current IFN therapies to threat HCV-infection.

3.1 DEFINITIONS

As used herein, the term "ISDR" or "interferon sensitivity determining region" refers to a domain of a protein having the amino acid sequence shown in FIG. 1A, or any derivative of that sequence, or fragments or peptides having that sequence, which has the activity of conferring IFN resistance or binding to IFN-induced PKR protein kinase.

As used herein, the term "PKR" or "IFN-induced PKR protein kinase" refers to the host cell protein kinase which is activated by interferon, also known as p68 kinase, P1, DAI, dsI or elF-1 kinase, and any derivative of PKR thereof, or fragments or peptides having the amino acid sequence corresponding to PKR.

As used herein, the term "screening" or "to screen" refers to a process in which a large number of potentially useful agents are processed in the methods of the invention.

As used herein, the term "to target" means to inhibit, block or prevent gene expression, enzymatic activity or interaction with other cellular or viral factors.

As used herein, the term "treating or preventing HCV infection" means to inhibit HCV transmission, or to prevent HCV from establishing itself in its host, and to ameliorate or alleviate the symptoms of the disease caused by HCV infection. The treatment is considered therapeutic if there is a reduction in viral load, decrease in mortality and/or morbidity.

As used herein, the term "treating or preventing viral infection" means to inhibit virus transmission, or to prevent the virus from establishing itself in its host, and to ameliorate or alleviate the symptoms of the disease caused by viral infection. The treatment is considered therapeutic if there is a reduction in viral load, decrease in mortality and/or morbidity.

As used herein, the term "pharmaceutically acceptable carrier" refers to a carrier medium that does not interfere with the effectiveness of the biological activity of the active ingredient, is chemically inert and is not toxic to the patient to whom it is administered.

The term "therapeutic agent" refers to any molecule compound or treatment, preferably an antiviral, that assists in the treatment of a viral infection or the diseases caused thereby.

4. BRIEF DESCRIPTION OF THE DRAWINGS

FIGS. 1A and 1B (A) Top panel, amino acid sequence comparison of the prototypic ISDR of NS5A from IFN-resistant HCV strain J and the corresponding region of NS5A from HCV strains 1a and 1b which were used in this study. Bottom panel, structural representation of HCV NS5A representing the 447 aa protein from HCV-1a and -1b strains contained in our NS5A constructs. The ISDR is indicated in black, and is deleted from the ISDR construct derived from HCV-1a. Amino acid positions within NS5A are shown in bold type, those corresponding to positions within the HCV polyprotein are shown in normal type.

(B) Structural representation of PKR. The position of the two dsRNA binding motifs within the regulatory domain are shown in black. The catalytic domain spans aa 265–551 and includes the 11 protein kinase catalytic domain conservation regions (Hanks et al., 1988, Science 241:42–52) indicated by roman numerals. The regions of interaction with the PKR-inhibitory molecules adenovirus VAI RNA, vaccinia virus K3L and $P_{58}^{IPK}$ are indicated (Katze et al., 1987, Embo J. 6:689–697; Gala Jr. et al., 1996, Mol. Cell. Biol. 16:4172–4181). Also indicated is the NS5A-binding region.

Figure 2:
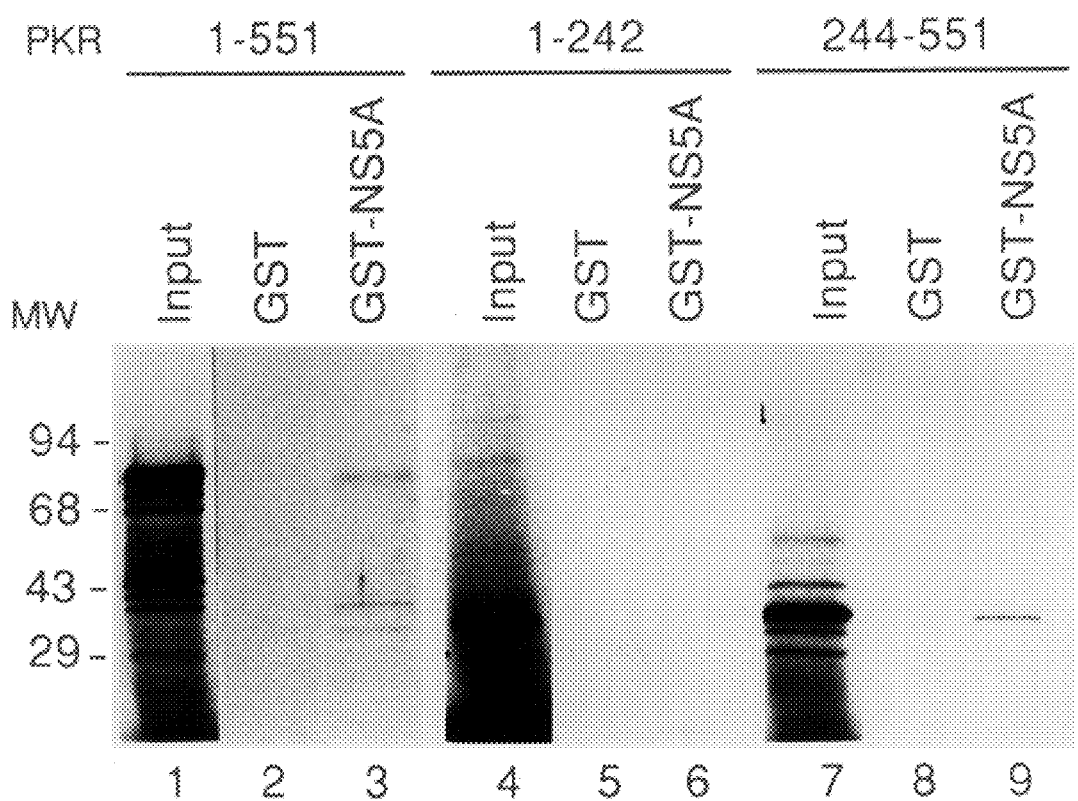

FIG. 2. In vitro binding analysis. FIG. 2 shows an autoradiogram of [$^{35}$S]-methionine-labeled PKR in vitro translation products alone (lanes 1,4 and 7) or selected by binding to GST or GST-NS5A within crude E. coli extracts, as indicated above each lane. Bound complexes containing PKR aa 1–5S1 (lanes 2 and 3), 1–242 (lanes 5 and 6), or 244–551 (lanes 8 and 9) were recovered by selection on glutathione-agarose. Bound translation products were eluted in SDS sample buffer and separated by 12.5% acrylamide SDS-PAGE. Arrow at right shows the position of PKR aa 244–251, which migrates below the background band visible in lanes 8 and 9. Positions of molecular mass standards are shown in kDa (left).

Figure 3:
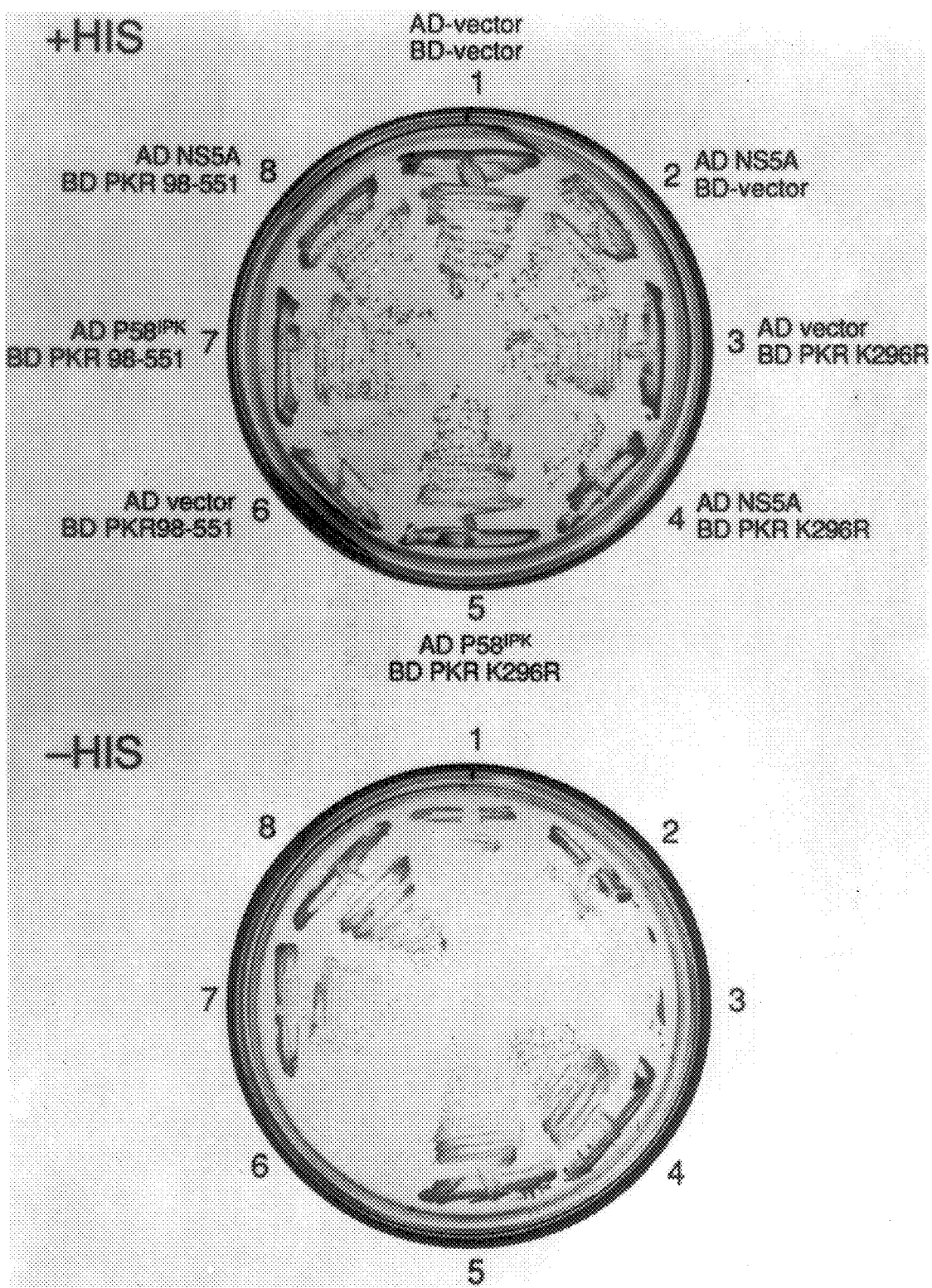

FIG. 3. Yeast 2-hybrid analysis. NS5A from HCV-1b interacts with PKR in vivo. Full length wt NS5A from HCV-1b was fused to the GAL4 transcription activation domain (AD) and coexpressed in yeast with the GAL4 DNA binding domain (BD) (position 2) or the BD-PKR fusion constructs BD-PKR K296R and BD-PKR 98–551 (positions 4 and 8, respectively). Coexpression of control GAL4 constructs for the 2-hybrid assay included AD-vector/BD-vector (position 1), AD-vector/BD-PKR K296R (position 3), AD-P58$^{IPK}$/BD-PKR K296R (position 5), AD-vector/BD PKR 98–551 (position 6) and ADP58$^{IPK}$/BD-PKR 98–551 (position 7). Transfected yeast were replica plated into +His (top) and –His medium (bottom). Growth on –His is indicative of 2-hybrid protein interaction.

Figure 4:
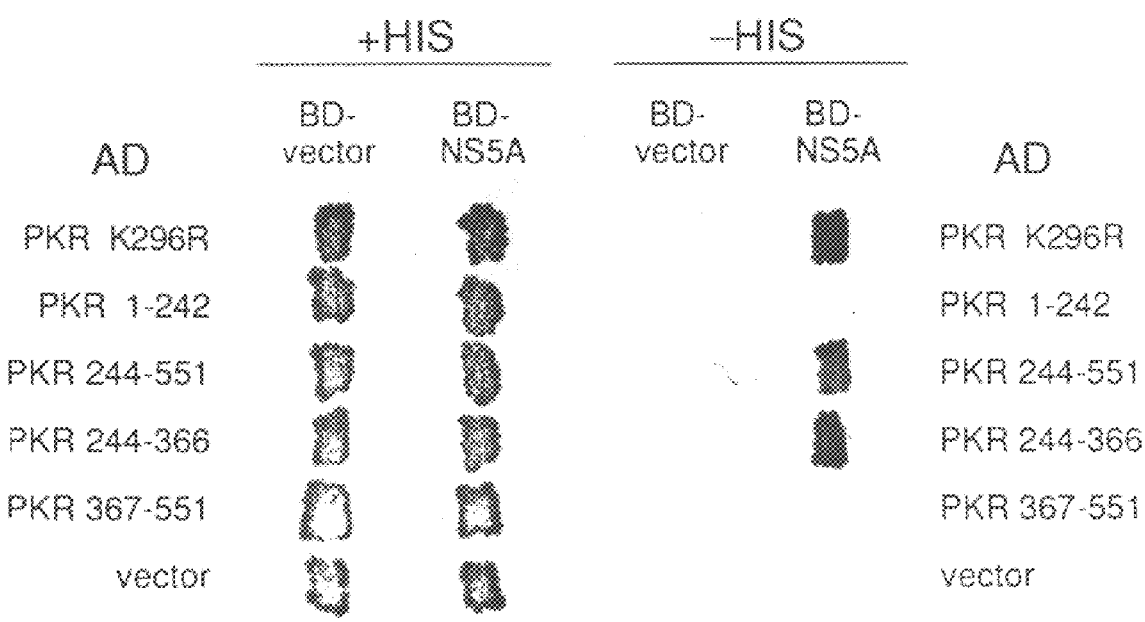

FIG. 4. NS5A from HCV-1a interacts with the PKR protein kinase catalytic domain. Yeast expressing either the BD alone (BD-vector) or a BD-NS5A fusion protein from HCV-1a (BD-NS5A) were cotransfected plasmids expressing the indicated AD-PKR fusion constructs or the control AD-vector (bottom row), replica plated onto +His (left) and –His medium (right) and assayed for growth.

Figure 5:
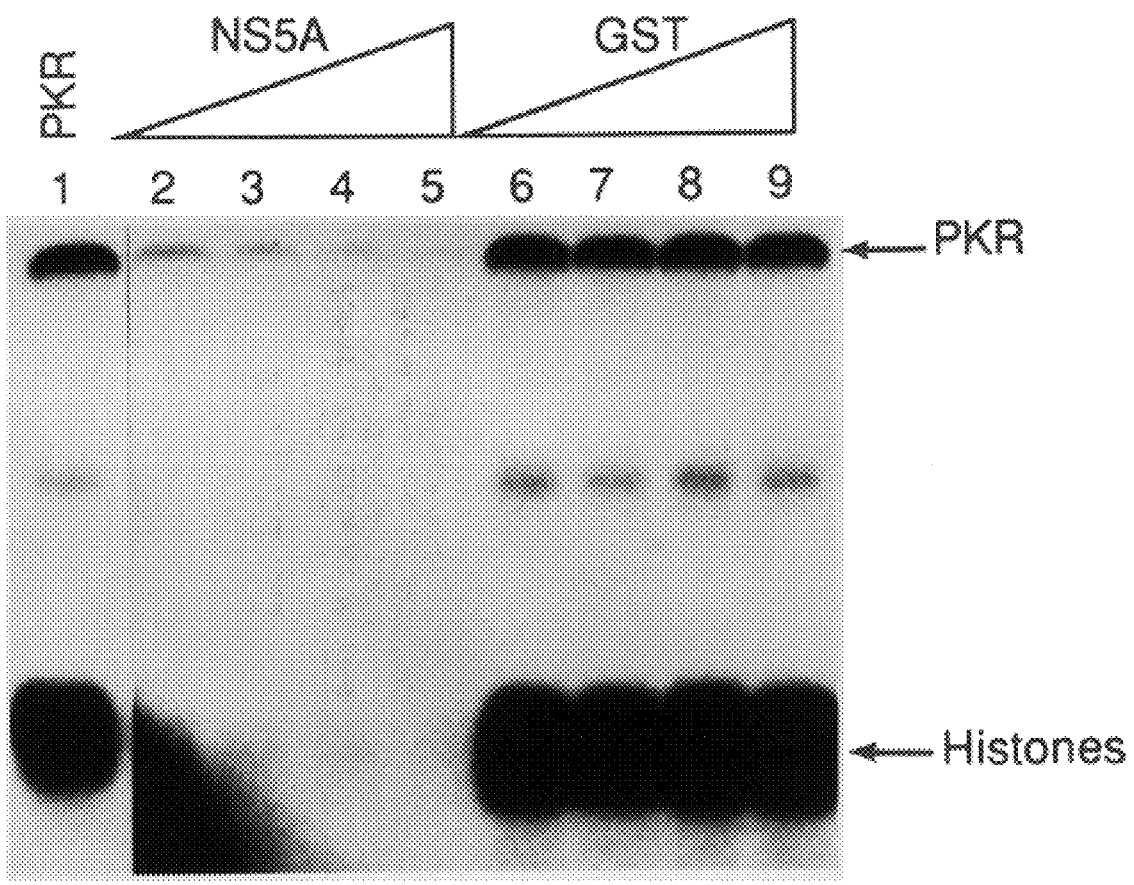

FIG. 5. Recombinant NS5A inhibits PKR activity in vitro. Purified native PKR (1.8 pmol) was preincubated with buffer (lane 1) or increasing amounts of recombinant purified GST-NS5A (HCV 1a, lanes 2–5) or GST (lanes 6–9) and assayed for in vitro kinase activity in the presence of histone H2a substrate. After termination of kinase reactions, phosphorylated products were separated by 12.5% SDS-PAGE and visualized by autoradiography of the dried gel. Arrows indicate the positions of PKR and histones. The molar amounts of input GST-NS5A or GST proteins were 0.2 pmol (lanes 2 and 6) 0.4 pmol (lanes 3 and 7), 0.8 pmol (lanes 4 and 8)and 1.2 pmol (lanes 5 and 9).

Figure 6:
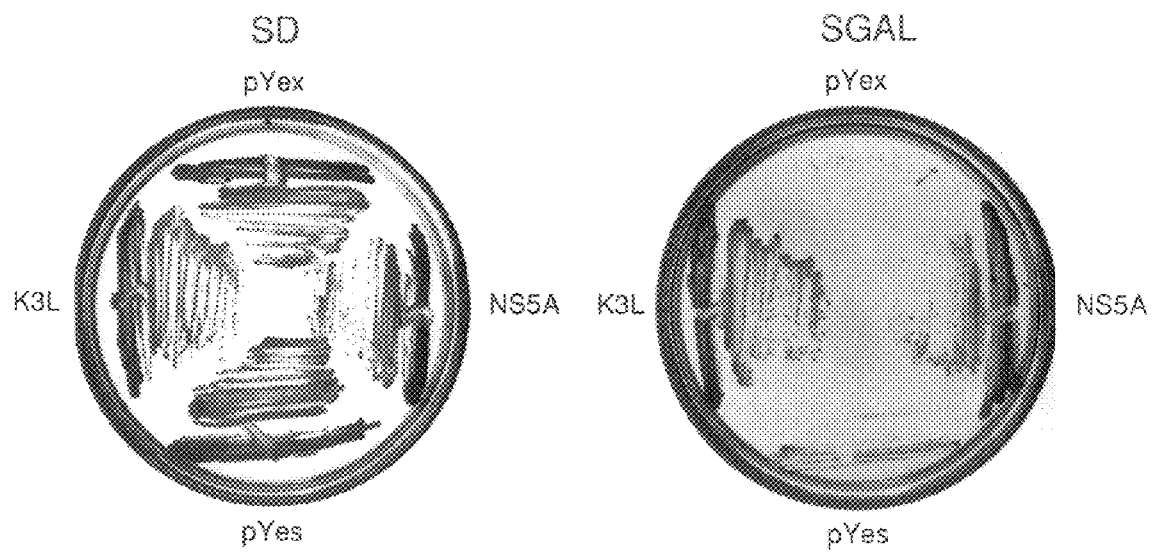

FIG. 6. NS5A reverses PKR-mediated growth suppression in yeast. Yeast strain RY1-1 was transfected with the 2m yeast expression constructs pYES2-NS5A (NS5A; from HCV-1a), pEMBLYex4K3L (vaccinia virus K3L; positive control) or the negative control vectors pEMBLYex4 (pYex) and pYes2 (pYes). Transfectants were plated onto minimal synthetic medium containing 2% dextrose (SD, left) or 10% galactose/2% raffinose (SGAL, right) as the carbon source and scored for growth. SGAL plate represents 5 days growth.

Figure 7:
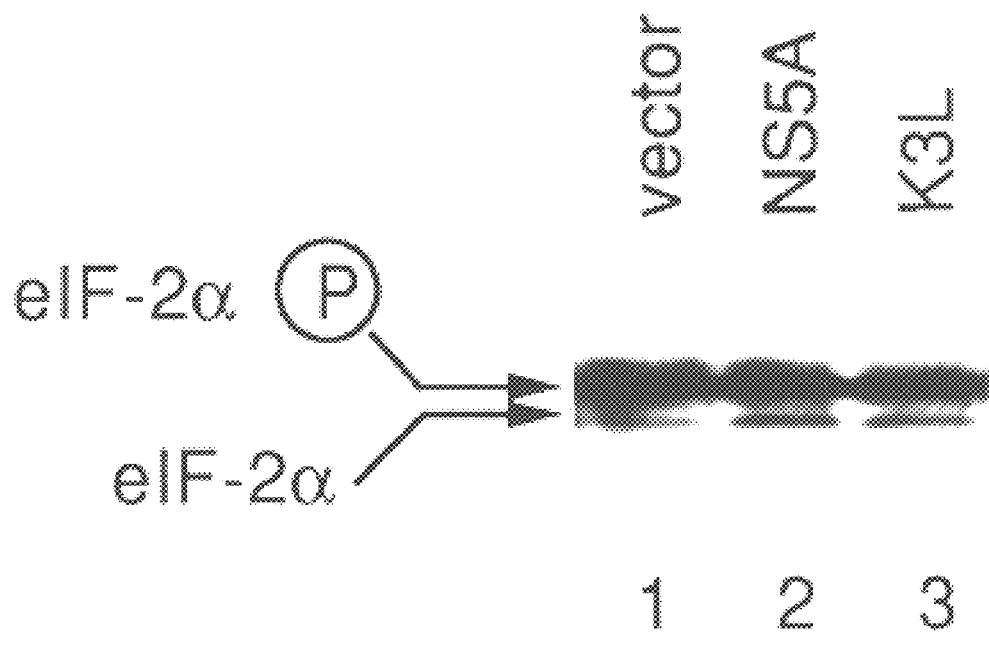

FIG. 7. eIF-2α phosphorylation analysis. Extracts from the yeast strains shown above were prepared and subjected to isoelectric focusing and immunoblot analyses as described Proteins (20 mg) were first separated by isoelectric focusing and then transferred to a nitrocellulose membrane which was subsequently probed with an antiserum specific to yeast eIF-2α. Arrows indicate the positions of basally phosphorylated eIF-2α (lower band) and eIF-2α phosphorylated in Ser 51, the site of phosphorylation by PKR (upper band). The levels of basally phosphorylated eIF-2α relative to total were quantitated by scanning laser densitometry and are: vector, 0.9% (lane 1); NS5A, 9.8% (lane 2) and K3L, 11.7% (lane 3).

Figure 8:
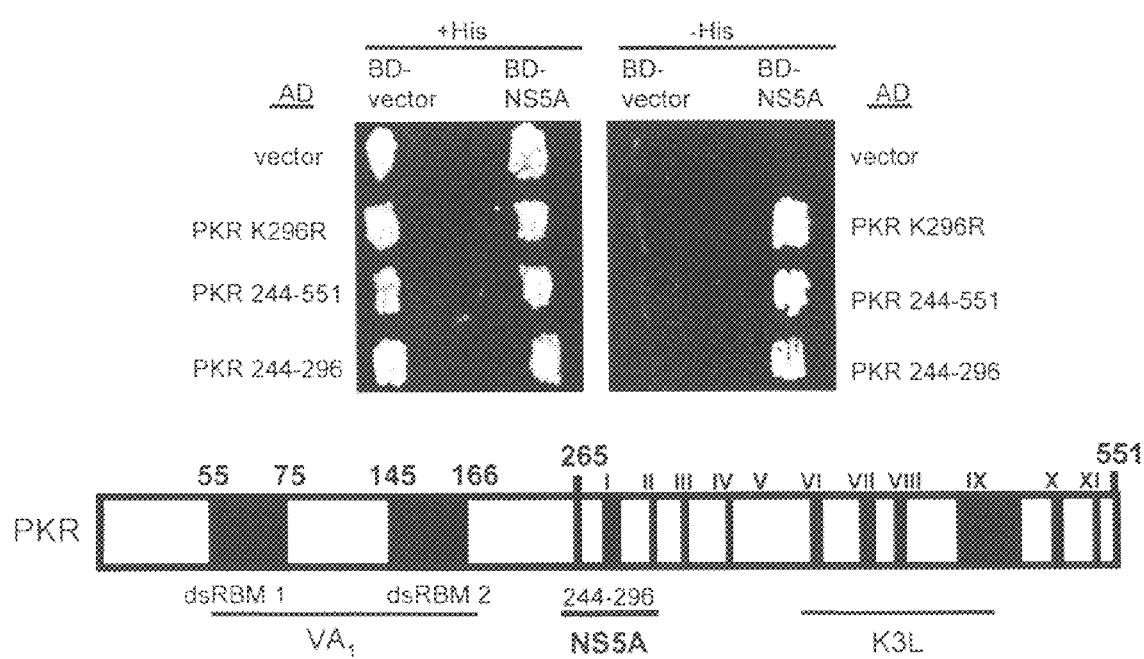

FIG. 8. The NS5A-binding domain of PKR. (Upper panel) Hf7c yeast strains harboring the indicated AD and BD expression constructs were replica printed onto +His (left) and –His (right) medium, incubated at 30° C. for 4 days and assayed for growth. Expression of AD-PKR and BD-NS5A 1b-wt constructs was confirmed by immunoblot analysis. Strains which grew on –His medium were scored positive for a 2-hybrid protein interaction. (Lower panel) The structural representation of PKR. The positions of the two dsRNA binding motifs (dsRBM) and the 11 protein kinase catalytic domain conservation regions (roman numerals) are indicated in black. The regions of PKR which mediate interaction with the viral-encoded inhibitors, adenovirus VA1, RNA, vaccinia virus K3L and HCV NS5A proteins are underlined.

Figure 9:
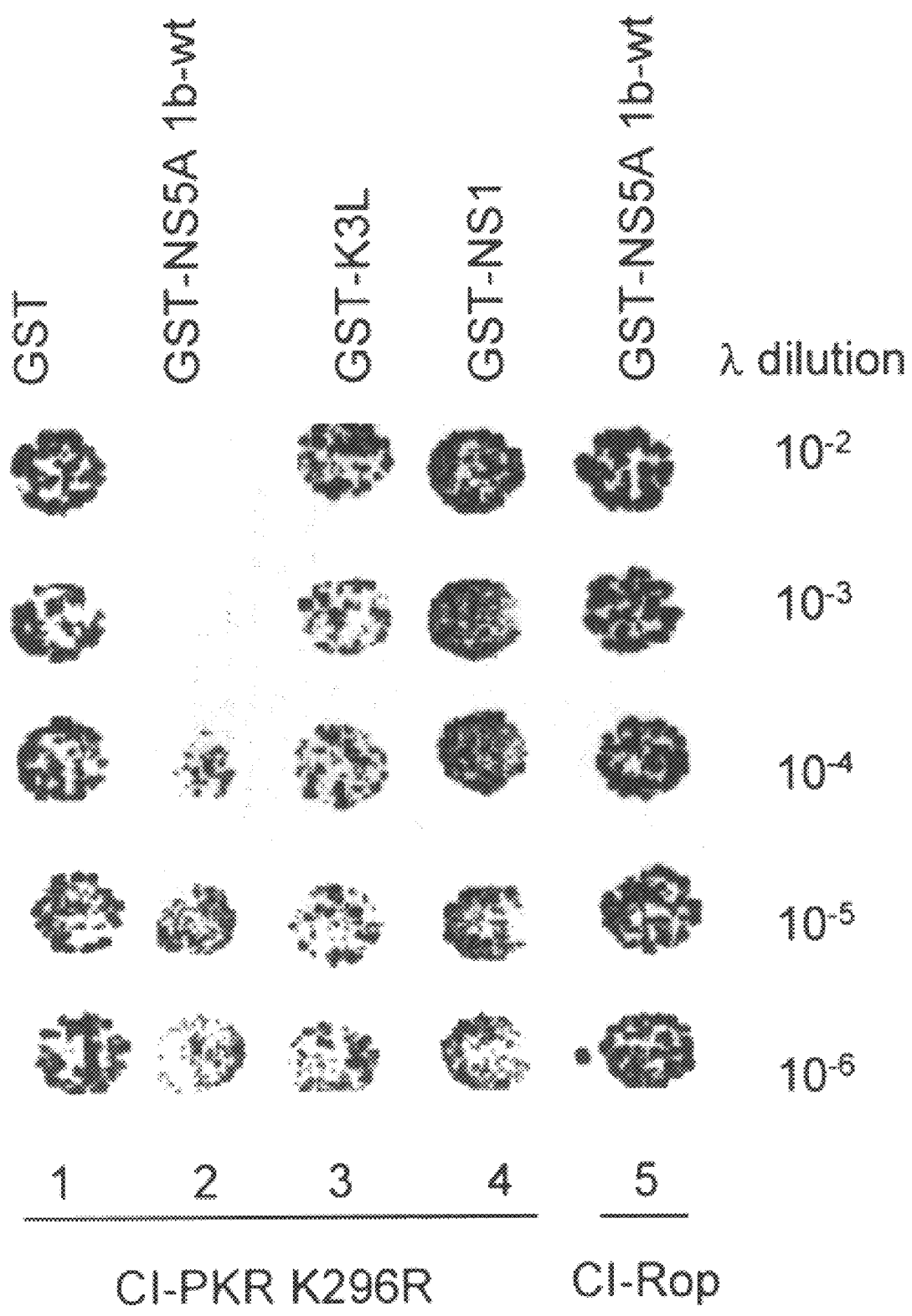

FIG. 9. NS5A disrupts PKR dimerization. AG1688 *E. coli* were co-transformed with expression plasmid combinations encoding CI-PKR K296R and GST (column 1), GST-NS5A 1b-wt (column 2), GST-K3L (column 3), or GST-NS1 (column 4), mixed with the indicated dilution of λKH54 phage, and spotted onto plates containing agar medium. Column 5 contains *E. coli* harboring CI-Rop and GST-NS5A 1b-wt expression plasmids (control). CI-fusion protein dimerization is indicated by colony formation.

Figure 10A:
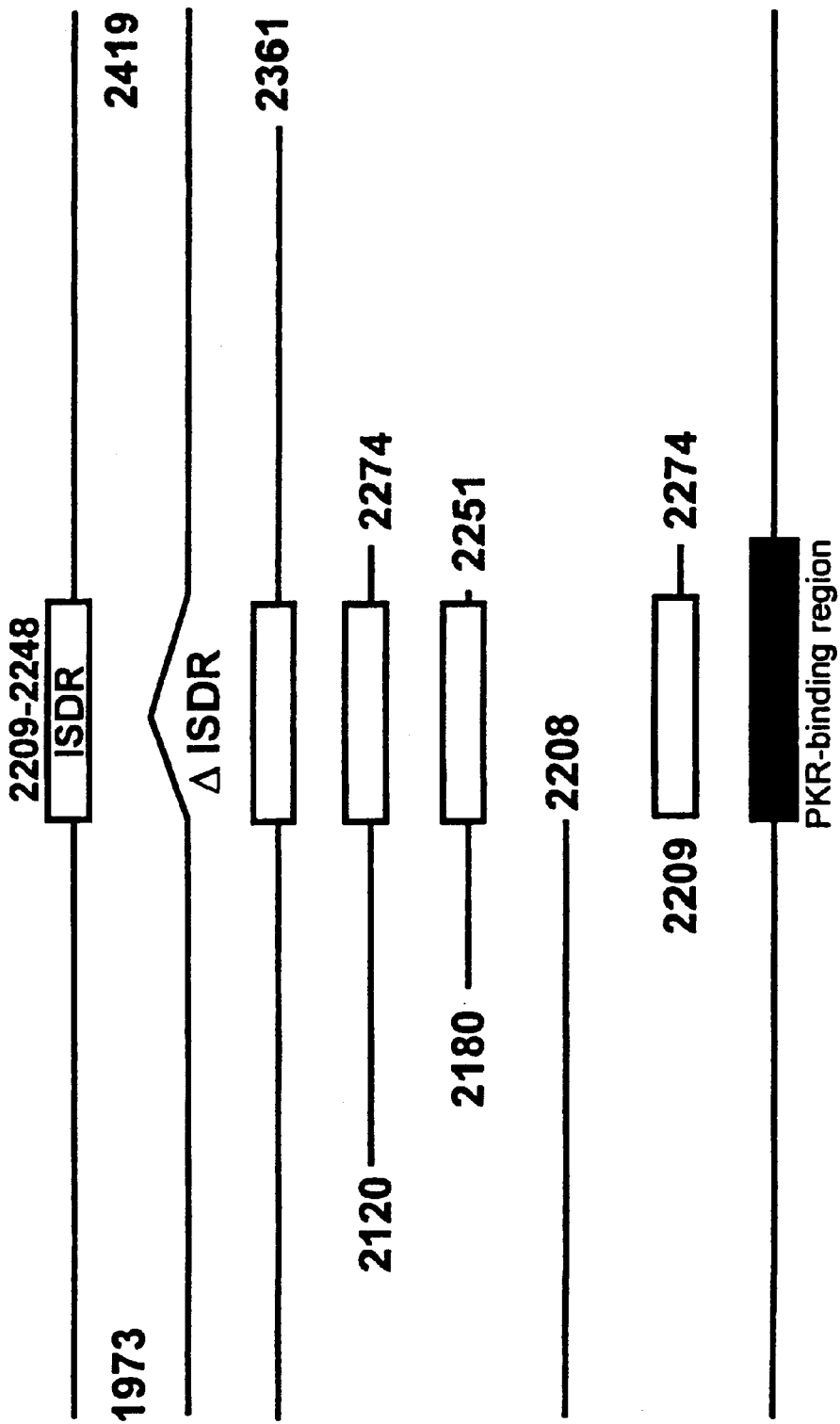
Figure 10C:
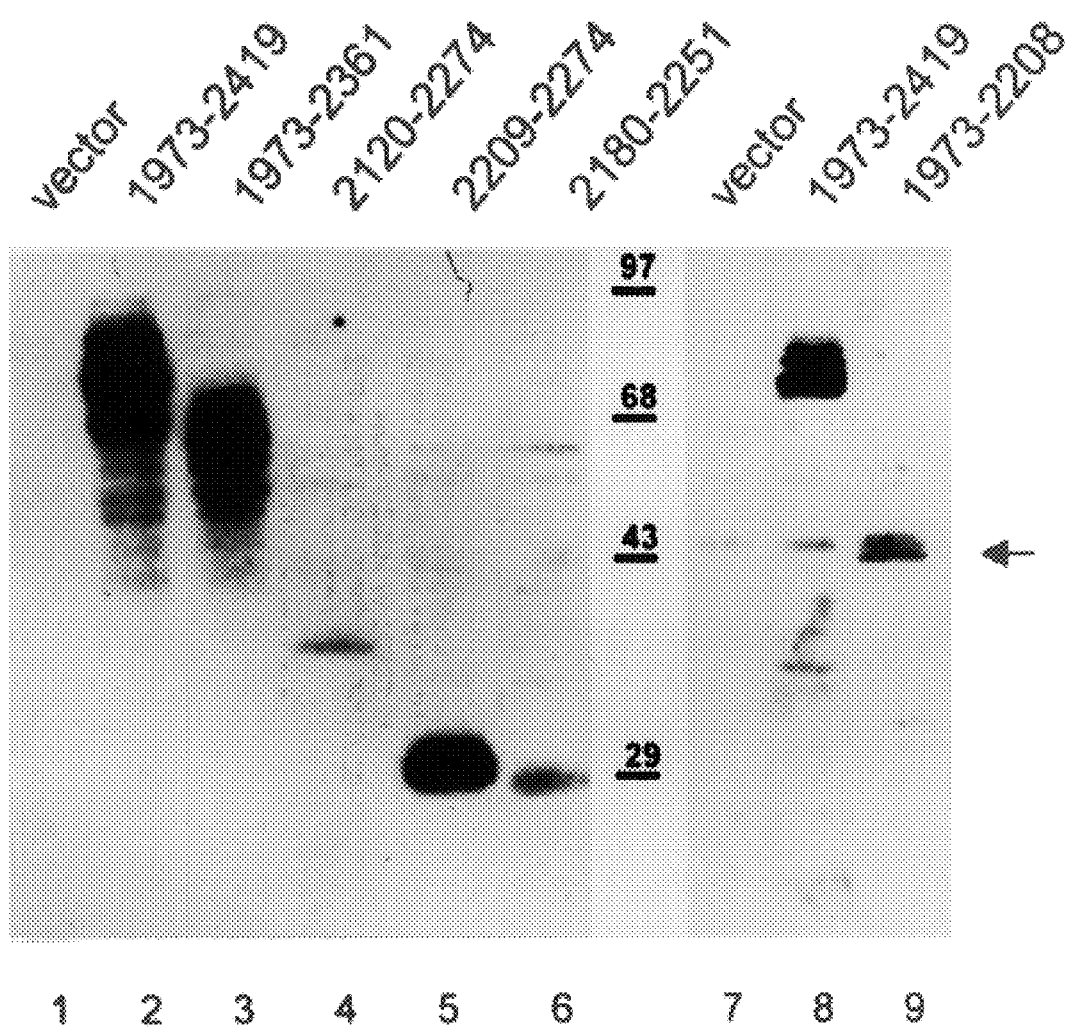

FIGS. 10A–10C. The PKR-binding domain of NS5A. FIG. 10A. Structural representation of GAL4 DNA binding domain-NS5A fusion constructs. Deletion mutants were prepared from NS5A 1b-wt, except for the ΔISDR construct which was prepared from NS5A 1a-wt. The ISDR and the PKR-binding region are shown as white and black rectangles, respectively. Terminal amino acid positions are indicated, with numbering based upon the prototypic HCV J polyprotein sequence. FIG. 10B. Yeast 2-hybrid assay Hf7c yeast harboring AD-PKR K296R were co-transformed with the indicated BD-NS5A deletion constructs. Shown is a −His plate incubated for three days at 30° C. Growth on −His medium is indicative of a 2-hybrid protein interaction. FIG. 10C. Immunoblot analysis. Extracts prepared from the yeast strains were separated by SDS-PAGE and subject to immunoblot analysis using anti-NS5A (lanes 1–6) or anti-BD (lanes 7–9) monoclonal antibody. Lanes 1 and 7 contain extracts prepared from strains harboring the pGBT9 BD-vector (control). Extracts are identified by the construct designation shown above each corresponding lane. BD-NS5A construct 1973–2419 was included as a positive control for the blot shown at right. Positions of protein standards are indicated in kDa.

Figure 11A:
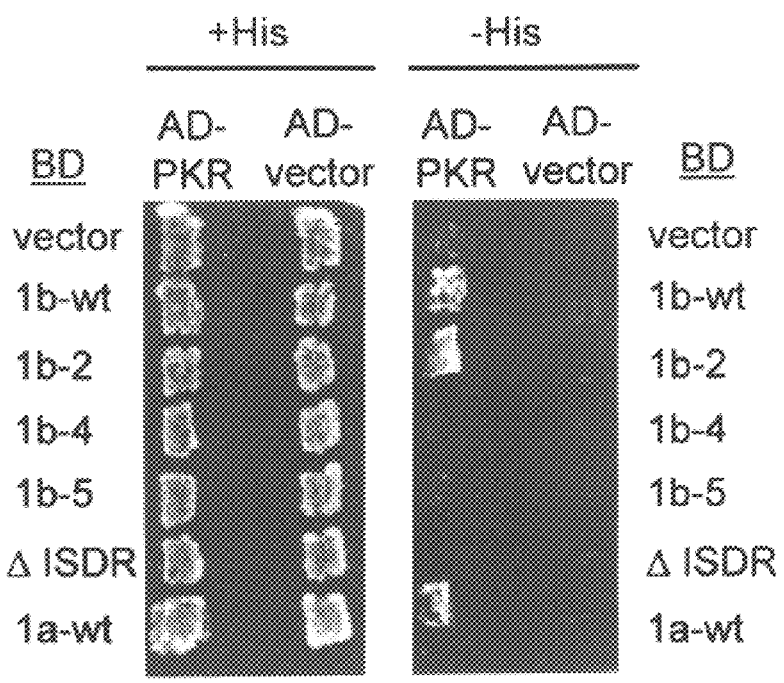
Figure 11B:
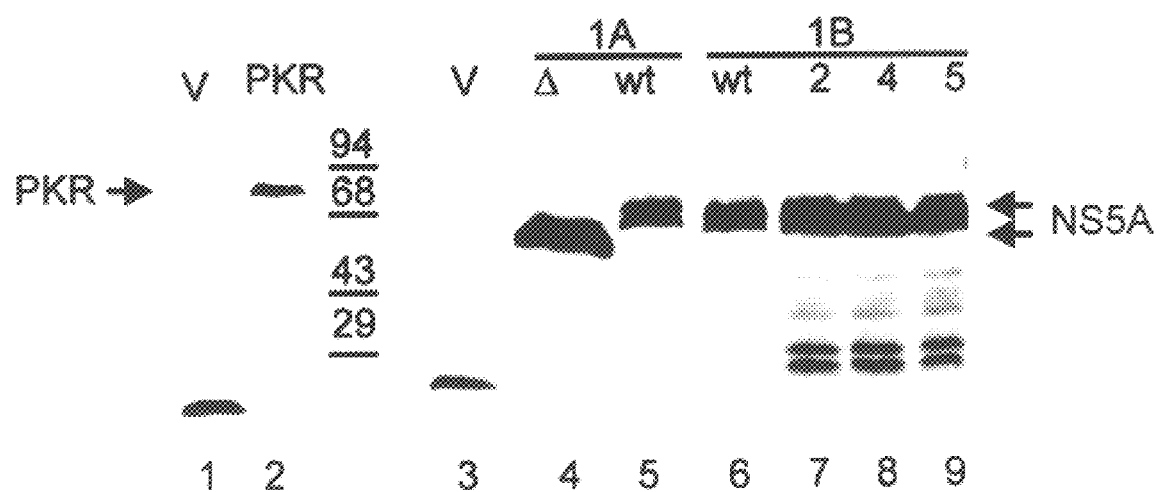

FIGS. 11A and 11B. Effect of ISDR mutations on the NS5A-PKR interaction. FIG. 11A. Yeast 2-hybrid assay. Hf7c yeast strains harboring pGAD425 encoding AD-PKR K296R (AD-PKR) or the AD alone (AD-vector) were co-transformed with pGBT9 encoding the BD alone (vector), BD-NS5A 1a-wt, BD-NS5A-ΔISDR, or an isogenic set of BD-NS5A 1b-wt constructs possessing the ISDR sequence shown in Table 1. Growth on −His medium is indicative of a 2-hybrid protein interaction. FIG. 11B. Immunoblot analysis. Extracts were prepared from the strains shown in A and subjected to immunoblot analysis using anti-AD (left panel) or anti-BD monoclonal antibody (right panel). Lanes 1 and 2 show expression of the AD-vector (v, control) and AD-PKR, (PKR; arrow), respectively. Lanes 3–9 show expression of the BD-vector (V, lane 3), BD-NS5AΔISDR (Δ, lane 4), BD-NS5A 1a-wt (wt, lane 5) BD-NS5A 1b-wt (wt, lane 6), BD-NS5A 1b-2 (2, lane 7), BD-NS5A 1b-4 (4, lane 8) and BD-NS5A 1b-5 (5, lane 9). Arrows at right indicate the positions of the ΔISDR and full-length BD-NS5A constructs. Positions of protein standards are shown in kDa.

Figure 12A:
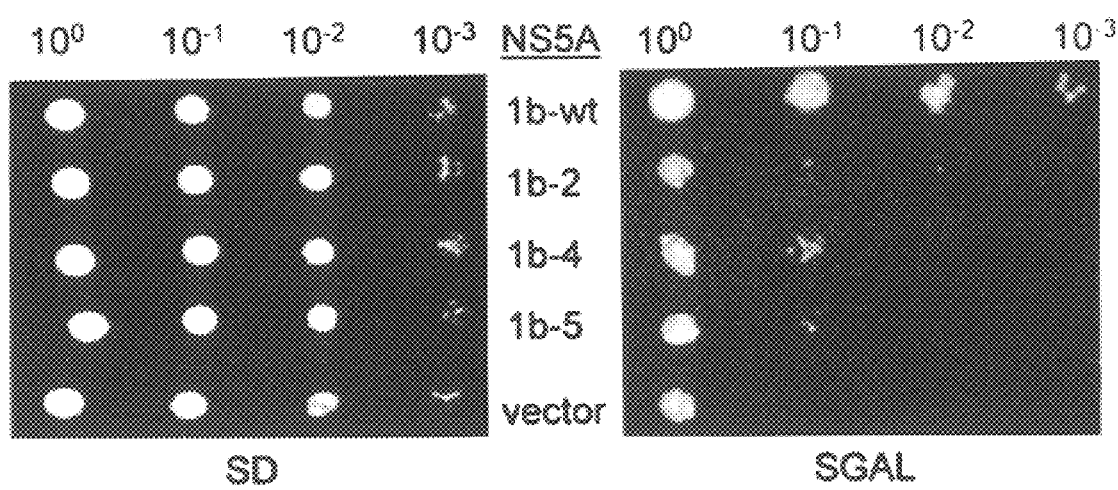
Figure 12B:
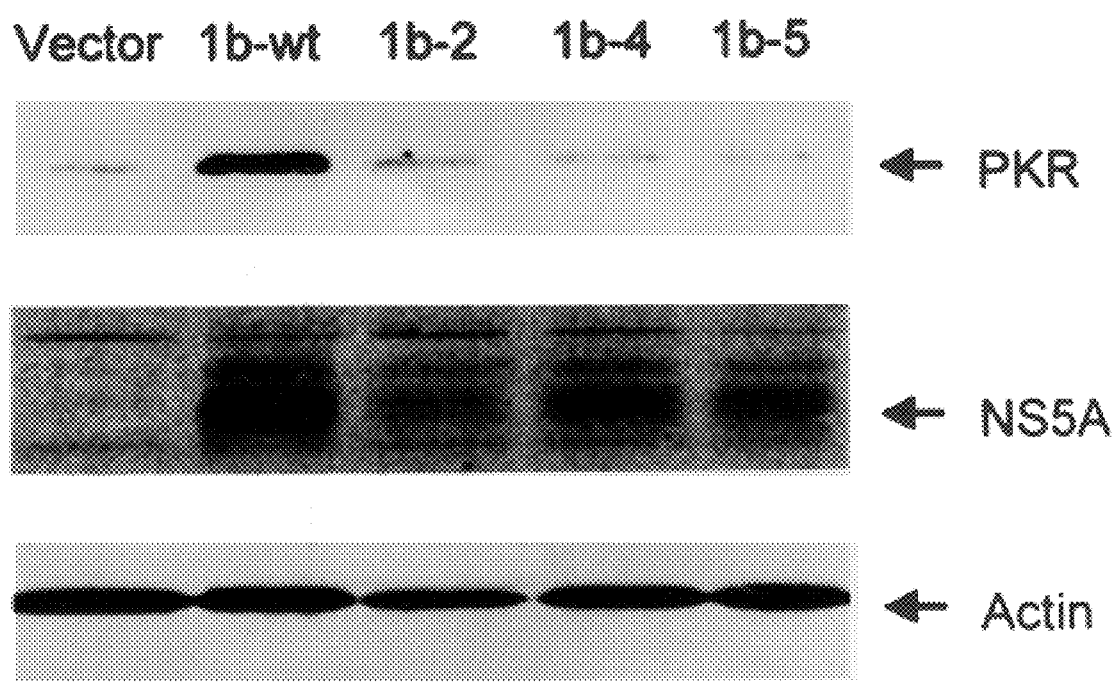

FIGS. 12A and 12B. ISDR mutations abolish NS5A function. FIG. 12A. Yeast growth assay. Cell equivalents of RY1-1 yeast strains harboring the galactose-inducible URA3 expression plasmids pYes-NS5A 1b-wt (1b-wt), pYes-NS5A 1b-2 (1b-2), pYes-NS5A 1b-4 (1b-4), pYes-NS5A 1b-5 (1b-5), or the pYes control (vector) were serially diluted and spotted onto medium containing dextrose (SD) or galactose (SGAL). Panels show colony formation after 5 days growth at 30° C. FIG. 12B. Immunoblot analysis of protein extracts prepared from the yeast strains shown in A. Shown are results derived from the same blot that was probed sequentially with anti-PKR, anti-NS5A, or anti-actin (control) monoclonal antibodies. Arrows at right denote the positions of PKR, NS5A and actin. Each lane represents 50 μg of total protein.

Figure 13:
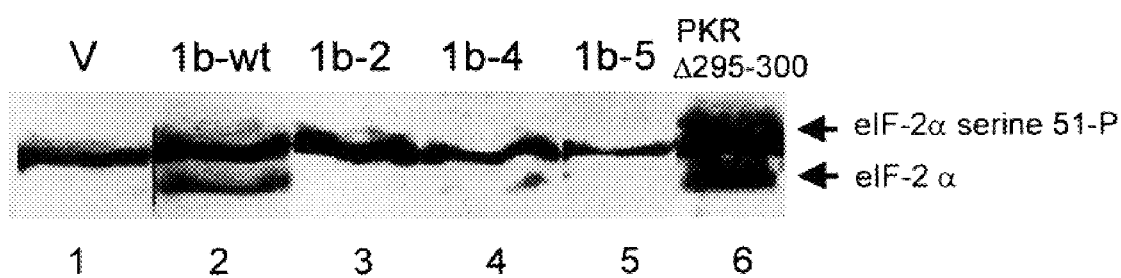

FIG. 13. eIF-2α phosphorylation. Detection of eIF-2α was facilitated by probing the blot with anti-yeast eIF-2α serum. Each lane represents 20 μg of protein prepared from RY1-1 strains harboring pYes (V, lane 1), pYes-NS5A 1b-wt (1b-wt, lane 2), pYes-NS5A 1b-2 (1b-2, lane 3), pYes-NS5A 1b-4 (1b-4, lane 4), pYes-NS5A 1b-5 (1b-5, lane 5) or pYex-PKR A295–300 [PKR A295–300 (control), lane 6]. Arrows at right show the positions of hypophosphorylated eIF-2α (lower) and hyperphosphorylated eIF-2α, which is phosphorylated by PKR on serine 51.

FIGS. 14A and 14B. ISDR mutations disrupt the NS5A-PKR association in mammalian cells. Cos-I cells were co-transfected with CMV expression plasmids encoding PKR K296R and NS5A, or PKR K296R and the vector control. Extracts were prepared and mixed with anti-NS5A monoclonal antibody (A) or anti-FLAG resin (B). FIG. 14A. Anti-NS5A immunocomplexes prepared from extracts harboring PKR K296R with vector control (neo, lane 1) or NS5A 1a-wt (1a-wt, lane 2), and input extract (IP-input, lanes 3 and 4) were separated by SDS-PAGE and subjected to immunoblot analysis using anti-PKR (lanes 1–3) or anti-NS5A (lane 4) monoclonal antibodies. Lanes 3 and 4 represents the starting material from the immunoprecipitation reaction shown in lane 2. The vertical line at left indicates the broad band corresponding to the inununoglobulin (Ig) heavy chain. Positions of protein standards are indicated in kDa. FIG. 14B. Immunoblot analysis of input protein (lanes 1–3) or protein complexes (lanes 4–6) recovered by mixing extracts harboring PKR K296R with vector alone (neo, lanes 1 and 4), FLAG-NS5A 1b-wt (1b-wt, lanes 2 and 5) or FLAG-NS5A 1b-5 (I b-5, lanes 3 and 6) with anti-FLAG resin. The blot was probed with a monoclonal antibody specific to human PKR. Arrow points to the PKR band.

Figure 15:
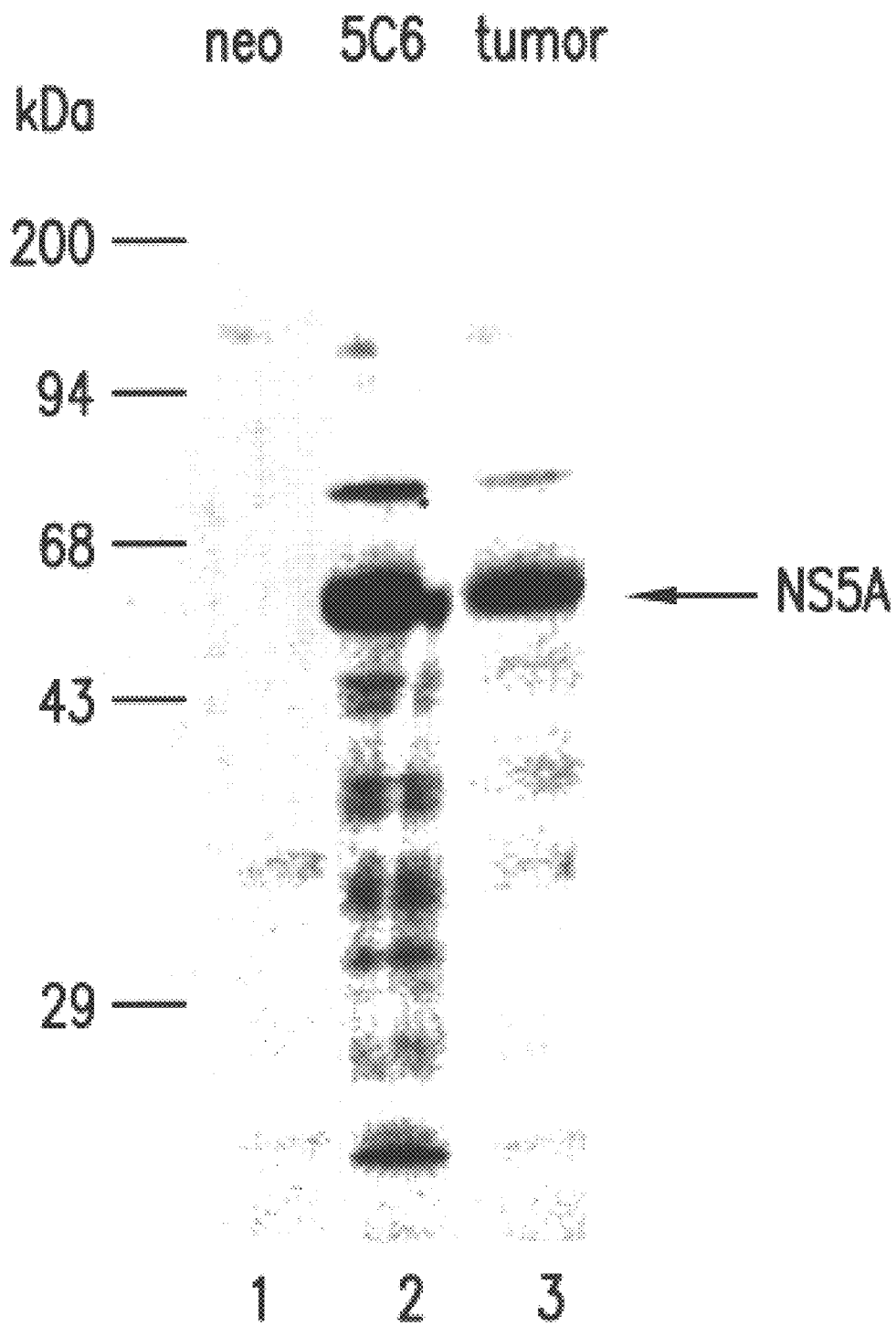

FIG. 15. Cell line and tumor expression of NS5A. Immunoblot of extracts prepared from NIH3T3 cell lines neo 5-10 (neo, lane 1) and NS5A 5C6 (5C6, lane 2),. or in vivo-derived NS5A 5C6 tumor cells (tumor, lane 3) probed with anti-NS5A monoclonal antibody. Arrow indicates the position of NS5A. Positions of protein standards are shown (kDa).

5. DETAILED DESCRIPTION OF THE INVENTION

The present invention relates to novel methods for identifying antiviral agents which interfere with viral inhibition of IFN-induced cellular defense mechanisms. The present invention relates to methods for screening for antiviral agents which target the interaction of viral proteins containing ISDR domains with cellular PKR protein kinase. The present invention more particularly relates to methods for screening for novel antiviral agents which target the interaction of HCV NS5A and IFN-induced PKR protein kinase. In another embodiment, the present invention more particularly relates to methods for screening for antiviral agents which target HCVNS5A inhibition of PKR dimerization.

The invention is based, in part, on the Applicants' surprising discovery that (1) the ISDR region of NS5A functionally contributes to the IFN-resistant phenotype of HCV; (2) additional sequences surrounding the ISDR are required for the interaction between NS5A and PKR; (3) NS5A represses IFN-induced PKR through a direct interaction with the protein kinase catalytic domain, in particular, amino acids 244–296; (4) PKR amino acids 244–296 is a dimerization domain and NS5A binding to this domain disrupts PKR dimerization; (5) the ISDR region is essential for both the interaction of NS5A with PKR, and the resulting inhibition of the protein kinase.

The present invention relates to screening assays to identify novel antiviral agents which target the interaction between viral proteins expressing an ISDR and IFN-induced cellular proteins, such as PKR protein kinase. The present invention further relates to screening assays to identify novel exogenous or endogenous agents that induce IFN-expression to a level that results in an override of NS5A inhibition of PKR protein kinase. The interaction of ISDR and IFN-induced PKR results in an override of IFN-induced cellular defense mechanisms, e.g., by inhibiting the dimerization of PKR, therefore, the screens of the invention which identify compounds that interfere with the interaction of viral proteins containing an ISDR and PKR, can be used to identify drugs that inhibit the viral override of host shut off of translation. Further, in identifying compounds that inhibit viral proteins containing an ISDR from interacting with cellular PKR, the screening assays of the present invention will also identify agents which inhibit the development of malignancies associated with viral infection. A variety of protocols and techniques may be utilized to screen for agents which interfere and/or inhibit the interaction between the ISDR of virally expressed proteins and IFN-induced PKR. Such identified agents would have utility in the treatment of hosts infected with viruses, and advantageously would be effective against IFN-resistant viruses.

The present invention further encompasses pharmaceutical compositions containing the novel agents identified by the screening assays described herein. The invention relates to therapeutic modalities and pharmaceutical compositions for the treatment of viral infections using ISDR containing proteins as the target for intervention. The present invention more particularly relates to therapeutic modalities and pharmaceutical compositions for the treatment of HCV-infection using NS5A and its interaction with IFN-induced PKR. Such therapeutics also have the advantage of making HCV increasingly susceptible to interferon and, thus, have utility in drug combinatorial treatments with IFN.

The therapeutic modalities of the invention further encompass combination therapies in which an agent which interferes with the interaction of NS5A and IFN-induced PKR, or an agent which induces levels of IFN-expression to a level that results in override of NS5A inhibition of PKR, and at least one other therapeutic agent are administered either concurrently, e.g., as an admixture, separately but simultaneously or concurrently; or sequentially, including cycling therapy. Cycling therapy involves the administration of a first antiviral compound for a period of time and repeating this sequential administration, i.e., the cycle, in order to reduce the development of resistance to one of the therapies.

The novel antiviral combinations of the present invention provide a means of treatment which may not only reduce the effective dose of either drug required for antiviral activity, thereby reducing toxicity, but may also improve the absolute antiviral effect as a result of attacking the virus through multiple mechanisms. Similarly, the novel antiviral combinations provide a means for circumventing the development of viral resistance to a single therapy, thereby providing the clinician with a more efficacious treatment. Therapeutic agents to be used in combination with an agent which targets the interaction between NS5A and PKR encompass a wide variety of known treatments, including α-IFN.

5.1 The Role of the Interaction Between HCV NS5A and IFN-induced PKR in HCV Infection The present invention is based, in part, on the Applicants' surprising discovery that (1) the ISDR region of NS5A functionally contributes to the IFN-resistant phenotype of strains of HCV; (2) NS5A represses IFN-induced PKR through a direct interaction with the protein kinase catalytic domain; and (3) both the inhibition of PKR and the interaction between NS5A and PKR requires the ISDR. These discoveries are exemplified in Sections 6, 7, 8 and 9 infra, which describe a combination of biochemical and genetic strategies demonstrating that NS5A represses PKR through a direct interaction.

The working examples described infra demonstrate the direct interaction between NS5A and PKR using in vitro GST binding assays and in vivo yeast two hybrid assays, NS5A was found to interact directly with the carboxyl, catalytic portion of the protein kinase i.e., PKR dimerization domain aa 244–296. Recombinant purified NS5A was shown to inhibit PKR kinase activity in vitro. Cotransfection studies in mammalian cells revealed that NS5A inhibited PKR dimerization in vivo resulting in repression of PKR function and inhibition of PKR-mediated eIF-2α phosphorylation. Further, when expressed in yeast NS5A was shown to inhibit the PKR-induced slow growth phenotype and reduce phosphorylation of PKR's natural substrate, eIF-2α. More importantly, NS5A deletion mutants lacking the ISDR were unable to interact with PKR or inhibit protein kinase activity. Further, the introduction of multiple ISDR mutations, found within interferon sensitive strains of HCV-1b, abrogated the ability of NS5A to bind PKR in mammalian cells. Interestingly, a single ISDR point mutation was sufficient to disrupt the PKRR regulatory function of NS5A, while still maintaining the ability to bind to PKR. The working examples further demonstrate that when cell lines overexpress NS5A they become malignantly transformed and caused tumors in nude mice. These results demonstrate, for the first time, that inactivation of PKR by the NS5A gene product is one mechanism by which HCV avoids the antiviral effects of IFN, and therefore, that this interaction serves as an important target in developing HCV antiviral therapeutics, in addition to therapeutics to treat malignancies which result from chronic HCV infection.

5.2 Production of HCV NS5A and PKR as Components for Screening Assays

The present invention relates to screening assays to identify those compounds which would target the interactions between NS5A and PKR, and more specifically the interactions between the ISDR and the catalytic domain of PKR. In one embodiment of the invention, an important component of the screening assays of the present invention are nucleotide coding sequences encoding viral NS5A and cellular PKR proteins, polypeptides and peptides. In particular, the present invention encompasses nucleotide coding sequences encoding peptide fragments corresponding to the ISDR and the catalytic domain of PKR protein kinase. The present invention further encompasses (a) DNA vectors that contain any of the foregoing NS5R or PKR encoding sequences and/or their complements; (b) DNA expression vectors that contain any of the foregoing NS5A or PKR coding sequences operatively associated with a regulatory element that directs the expression of the coding sequences in the host cell; and (c) genetically engineered host cells that contain any of the foregoing NS5A or PKR coding sequences operatively associated with a regulatory element that directs the expression of the coding sequences in the host cell.

5.2.1 The NS5A and PKR Coding Sequences

The invention encompasses nucleotide coding sequences that encode NS5A proteins, peptide fragments of the NS5A protein and NS5A fusion proteins. In a preferred embodiment, the invention encompasses nucleotide coding sequences encoding the ISDR amino acid sequence as shown in FIG. 1A, peptide fragment and fusion proteins containing that amino acid sequence. In yet another preferred embodiment, the present encompasses nucleotide coding sequences that also encode those sequences carboxyl to the ISDR which are also required for interaction with the PKR, and peptide fragments and fusion proteins that comprise the amino acid sequence encoded by these nucleotide coding sequences. In a further embodiment, the present invention encompasses nucleotide sequences which encode multiple ISDR mutations found within IFN-sensitive strains of HCCV, and peptide fragments and fusion proteins that comprise these ISDR mutants.

The invention further encompasses nucleotide coding sequences that encode PKR protein kinase, peptide fragments of the PKR protein kinase and PKR protein fusion proteins. In a preferred embodiment, the invention encompasses nucleotide coding sequences encoding the catalytic domain of PKR and fusion proteins containing the catalytic domain of PKR. In yet another preferred embodiment, the invention encompasses nucleotide coding sequences comprising the PKR dimerization domain, amino acids 244 to 246, and peptide fragments and fusion proteins containing PKR amino acids 244 to 296.

Nucleotides encoding fusion proteins may include but are not limited to full length NSDR or PKR, truncated proteins or peptide fragments of NSDR or PKR fused to an unrelated protein or peptide, such as for example, the ISDR fused to a GST or an enzyme or fluorescent protein.

The invention also encompasses (a) DNA vectors that contain any of the foregoing NS5A or PKR protein kinase coding sequences and/or their complements (i.e., antisense); (b) DNA expression vectors that contain any of the foregoing NS5A or PKR protein kinase coding sequences operatively associated with a regulatory element that directs the expression of the coding sequences; and (c) genetically engineered host cells that contain any of the foregoing NS5A or PKR protein kinase coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to inducible promoters, such as heat shock promoters, galactose inducible promoters, viral promoters, such as the promoter of tobacco mosaic virus (TMV), cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

5.2.2 NS5A And PKR Proteins And Polypeptides

NS5A and PKR proteins, polypeptides, peptide fragments, mutated, truncated or deleted forms of the NS5A and PKR proteins and fusion proteins containing the ISDR or the catalytic domain of PKR may be generated for a variety of uses, including, but not limited to the generation of antibodies, the identification of other factors involved in viral by-pass of the IFN-induced cellular defense mechanisms.

Mutations may be made to NS5A and PKR coding sequence to generate proteins and peptides that are better suited for expression, scale up, etc. in the host cells chosen.

Peptides corresponding to one or more domains of the target, truncated or deleted NS5A or PKR proteins including ISDR and the catalytic domain of PKR, as well as fusion proteins in which the full length NS5A or PKR is fused to an unrelated protein are also within the scope of the invention. Such fusion proteins include but are not limited to IgFc fusion which stabilize the NS5A or PKR protein or peptide and prolong half-life in vivo; GST fusion or fusions to any amino acid sequence that allows the fusion protein to be anchored to a solid support, or that allowing the ISDR to be exhibited on the stable surface; or fusions to an enzyme, fluorescent protein, or luminescent protein which provide a marker function.

While the polypeptides and peptides of the present invention can be chemically synthesized (e.g., see Creighton, 1983, Proteins: Structures and Molecular Principles, W. H. Freeman & Co., N.Y.), large polypeptides derived from the NS5A and PKR coding sequences may advantageously be produced by recombinant DNA technology using techniques well known in the art for expressing nucleic acid containing the NS5A and PKR coding sequences and/or coding sequences. Such methods can be used to construct expression vectors containing the nucleotide sequences described in Section 5.2.1 and appropriate transcriptional and translational control signals. These methods include, for example, in vitro recombinant DNA techniques, synthetic techniques, and genetic recombination. See, for example, the techniques described in Sambrook et al., 1989, supra, and Ausubel et al., 1989, supra. Alternatively, RNA capable of encoding NS5A or PKR nucleotide sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the NS5A and PKR nucleotide sequences of the invention.

Methods which are well known to those skilled in the art can be used to construct expression vectors containing the NS5A and PKR coding sequence and appropriate transcriptional/translational control signals. These methods include in vitro recombinant DNA techniques, synthetic techniques and in vivo recombination/genetic recombination. See, for example, the techniques described in Maniatis et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the NS5A and PKR coding sequence. These include but are not limited to microorganisms such as bacteria transformed with recombinant bacteriophage DNA, plasmid DNA or cosmid DNA expression vectors containing the NS5A and PKR coding sequence; yeast transformed with recombinant yeast expression vectors containing the NS5A and PKR coding sequence; insect cell systems infected with recombinant virus expression vectors (e.g., baculovirus) containing the NS5A and PKR coding sequence; NS5A and PKR cell systems infected with recombinant virus expression vectors (e.g., cauliflower mosaic virus, CaMV; tobacco mosaic virus, TMV) or transformed with recombinant plasmid expression vectors (e.g., Ti plasmid) containing the NS5A and PKR coding sequence; or animal cell systems infected with recombinant virus expression vectors (e.g., adenovirus, vaccinia virus).

The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the NS5A or PKR DNA SV40-, BPV- and EBV-based vectors may be used with an appropriate selectable marker.

In bacterial systems a number of expression vectors may be advantageously selected depending upon the use intended for the NS5A and PKR expressed. For example, when large quantities of NS5A and PKR are to be produced for the generation of antibodies or to screen peptide libraries, vectors which direct the expression of high levels of fusion protein products that are readily purified may be desirable. Such vectors include but are not limited to the *E. coli* expression vector pUR278 (Ruther et al., 1983, EMBO J. 2:1791), in which the NS5A and PKR coding sequence may be ligated into the vector in frame with the lac Z coding region so that a hybrid NS5A and PKR lac Z protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned polypeptide of interest can be released from the GST moiety.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516–544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II.

For long-term, high-yield production of recombinant proteins, stable expression is preferred. For example, cell lines which stably express NS5A or PKR may be engineered. In a preferred embodiment of the invention, yeast cells which stably express NS5A and PKR may be engineered. Such cell lines may serve as an in vivo system to screen for inhibitors of NS5A inhibition of PKR. Rather than using expression vectors which contain viral origins of replication, yeast host cells can be transformed with the NS5A and PKR DNA controlled by appropriate expression control elements (e.g., promoter, enhancer, sequences, transcription terminators, polyadenylation sites, etc.), and a selectable marker. In addition such host cells may also be transformed with DNA encoding a reporter gene whose expression is increased in response to activation of the PKR kinase. An example of such a reporter gene would be the GCN4 promoter fused to a β-galactose reporter gene. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NS5A gene, the PKR gene in addition to a reporter gene whose expression is increased in response to activation of the PKR protein kinase. Such engineered cell lines are particularly useful in screening for inhibitors of NS5A.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk$^-$, hgprt$^-$ or aprt cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin genes (Santerre, et al., 1984, Gene 30:147). Recently, additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.). The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression.

Further, previously unknown ISDR containing gene-type sequences may be isolated by performing PCR using two degenerate oligonucleotide primer pools designed on the basis of amino acid sequences within the gene of interest or using the PCR primers described in Section 6.1. The template for the reaction may be cDNA obtained by reverse transcription of mRNA prepared from cell lines or tissue infected with viruses known or suspected to express proteins containing ISDRs.

The PCR product may be subdloned and sequenced to ensure that the amplified sequences represent the sequences of an NS5A or ISDR gene-like nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to screen a genomic library.

PCR technology may also be utilized to isolate full length cDNA sequences. For example, RNA may be isolated, following standard procedures, from an appropriate cellular or tissue source. A reverse transcription reaction may be performed on the RNA using an oligonucleotide primer specific for the most 5'end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

In cases where the ISDR sequence identified is the normal, or wild type gene, this gene may be used to isolate mutant alleles of the gene. Mutant alleles may be isolated from viruses either known or proposed to have an IFN-resistant phenotype which contributes to its infectivity. Mutant alleles and mutant allele products may then be utilized in the development of in vitro assays, expression systems, and screening assays as described below.

A cDNA of the mutant gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from cells infected with a virus which is resistant to IFN and therefore would be suspected of expressing a gene containing an ISDR or a mutant thereof. The normal gene or any suitable fragment thereof may then be labeled and used as a probed to identify the corresponding mutant allele in the library. The clone containing this gene may then be purified and subjected to sequence analysis according to methods well known to those of skill in the art.

Additionally, an expression library can be constructed utilizing DNA isolated from or cDNA synthesized from cells or tissues infected with an IFN-resistant virus suspected of expressing the gene of interest in an individual suspected of or known to carry the mutant allele. In this manner, gene products made by the putatively mutant tissue may be expressed and screened using standard antibody screening techniques in conjunction with antibodies raised against the normal gene product, as described, below, in Section 5.3. (For screening techniques, see, for example, Harlow, E. and Lane, eds., 1988, "Antibodies: A Laboratory Manual", Cold Spring Harbor Press, Cold Spring Harbor.) In cases where the mutation results in an expressed gene product with altered function (e.g., as a result of a missense mutation), a polyclonal set of antibodies are likely to cross-react with the mutant gene product. Library clones detected via their reaction with such labeled antibodies can be purified and subjected to sequence analysis according to methods well known to those of skill in the art.

5.2.3 HOST CELLS AND EXPRESSION SYSTEMS

The host cells which contain the NS5A and PKR coding sequence and which express the biologically active gene product may be identified by at least four general approaches: (a) DNA-DNA or DNA-RNA hybridization; (b) the presence or absence of "marker" gene functions; (c) assessing the level of transcription as measured by the expression of NS5A and PKR mRNA transcripts in the host cell; and (d) detection of the gene product as measured by immunoassay or by its biological activity.

In the first approach, the presence of the coding NS5A and PKR sequence inserted in the expression vector can be detected by DNA-DNA or DNA-RNA hybridization using probes comprising nucleotide sequences that are homologous to the NS5A and PKR coding sequence or portions or derivatives thereof.

In the second approach, the recombinant expression vector/host system can be identified and selected based upon the presence or absence of certain "marker" gene functions (e.g., thymidine activity, resistance to antibiotics, resistance to methotrexate, transformation phenotype, occlusion body formation in baculovirus, etc.). For example, if the NS5A and PKR coding sequence is within a marker gene sequence of the vector, recombinants containing the NS5A and PKR coding sequence can be identified by the absence of the marker gene function. Alternatively, a marker gene can be placed in tandem with the NS5A and PKR sequence under the control of the same or different promoter used to control the expression of the NS5A and PKR coding sequence. Expression of the marker in response to induction or selection indicates expression of the NS5A and PKR coding sequence.

In the third approach, transcriptional activity for the NS5A and PKR coding region can be assessed by hybridization assays. For example, RNA can be isolated and analyzed by Northern blot using a probe homologous to the NS5R and PKR coding sequence or particular portions thereof. Alternatively, total nucleic acids of the host cell may be extracted and assayed for hybridization to such probes.

In the fourth approach, the expression of the NS5A and PKR protein product can be assessed immunologically, for example by Western blots, immunoassays such as radioimmuno-precipitation, enzyme-linked immunoassays and the like. The ultimate test of the success of the expression system, however, involves the detection of the biologically active NS5A and PKR gene product. Where the host cell secretes the gene product, the cell free media obtained from the cultured transfectant host cell may be assayed for NS5A and PKR activity. Where the gene product is not secreted, cell lysates may be assayed for such activity. In either case, a number of assays can be used to detect NS5A and PKR activity including but not limited to the following: cycloxygenase activity may be determined in the culture medium by the addition of exogenous arachidonic acid substrate (30 $\mu$M for 15 min. at 37° C.) followed by conversion of the prostagalandin $E_2$ product to a methyl oximate form. This bicyclic derivative may then be quantitated by radioimmunoassay (kit from Amersham Corp).

Desired NS5A and PKR cells may be obtained by engineering the gene constructs described herein into a variety of NS5A and PKR cell types, including but not limited to, tissue culture cells, mammalian cells, yeast cells, tissue and organ explants, embryos as well as whole animals. In an embodiment of the present invention, the engineered material is selected or screened for transformants (i.e., those that have incorporated or integrated the introduced gene construct(s)) following the approaches and methods described below.

A transformed cell, tissue or animal may be identified and isolated by selecting or screening the engineered material for traits encoded by the marker genes present on the transforming DNA. For instance, selection may be performed by growing the engineered cells on media containing inhibitory amounts of the antibiotic to which the transforming marker gene construct confers resistance. Further, transformed cells may also be identified by screening for the activities of any visible marker genes (e.g., the β-glucuronidase, luciferase, B or C1 genes) that may be present on the recombinant nucleic acid constructs of the present invention. Such selection and screening methodologies are well known to those skilled in the art.

Physical and biochemical methods also may be used to identify a cell transformant containing the gene constructs of the present invention. These methods include but are not limited to: 1) Southern analysis or PCR amplification for detecting and determining the structure of the recombinant DNA insert; 2) Northern blot, S-1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, western blot techniques, immunoprecipitation, or enzyme-linked immunoassays, where the gene construct products are proteins; 5) biochemical measurements of compounds produced as a consequence of the expression of the introduced gene constructs. Additional techniques, such as in situ hybridization, enzyme staining, and immunostaining, also may be used to detect the presence or expression of the recombinant construct in specific cells, organs and tissues. The methods for doing all these assays are well known to those skilled in the arts.

5.2.4 Purification of the NS5A or PKR Gene Product

Once a cell that produces high levels of biologically active NS5A or PKR is identified, the cell may be clonally expanded and used to produce large quantities of these proteins. The gene products may be purified using techniques well-known in the art including, but not limited to, immunoaffinity purification, chromatographic methods including high performance liquid chromatography and the like. Where the gene product is secreted by the cultured cells, NS5A or PKR polypeptides or peptides may be readily recovered from the culture medium.

Where the NS5A or PKR coding sequence has been engineered to encode a cleavable fusion protein, the purification of NS5A or PKR may be readily accomplished using affinity purification techniques. For example, an antibody specific for the heterologous peptide or protein can be used to capture the durable fusion protein; for example, on a solid surface, a column etc. The NS5A or PKR moiety can be released by treatment with the appropriate enzyme that cleaves the linkage site.

The ease of cDNA construction using the polymerase chain reaction, transfection and purification of the expressed protein permits the isolation of small, but sufficient amount of NS5A or PKR for characterization of the protein's physical and kinetic properties. Using site-directed mutagenesis or naturally occurring mutant sequences, this system provides a reasonable approach to determine the effects of the altered primary structure on the function of the protein. Fusion constructs having the domain of NS5A or PKR preceding the amino terminus of the cleavable protein versus constructs having the opposite arrangement, may also be engineered to evaluate which fusion construct will interfere the least, if at all, with the protein's biologic function and the ability to be purified.

Using this aspect of the invention, any cleavage site or enzyme cleavage substrate may be engineered between the NS5A or PKR sequence and a second peptide or protein that has a binding partner which could be used for purification, e.g, any antigen for which an immunoaffinity column can be prepared.

5.3 Antibodies to NS5A Proteins

Antibodies that define the NS5A gene product are within the scope of this invention, and include antibodies capable of specifically recognizing one or more NS5A gene product epitopes, such as the ISDR. Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of an NS5A gene product in a biological sample, including, but not limited to, blood plasma and serum. Alternatively, the antibodies may be used as a method for the inhibition of NS5A gene product activity.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NS5A gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

5.4 Screening Assays to Identity Agents which Selectively Inhibit the Interaction of NS5A and IFN-induced PKR The present invention relates to in vitro and in vivo methods for screening for agents which target viral proteins containing an ISDR and the interaction of these proteins with IFN-induced PKR protein kinase.

Methods to screen potential agents for their ability to disrupt or moderate viral effects on translation can be designed based on the Applicants' discovery that NS5A directly interacts with PKR and that the ISDR and catalytic domain of PKR are required for this interaction. Methods to screen potential agents for their ability to disrupt or moderate viral effects can be further designed based on the Applicant's discovery that NS5A binds to PKR dimerization domain, amino acids 244–296, resulting in inhibition and repression of PKR function. In principle, many methods known to those of skill in the art, can be readily adapted to detect interference with the interaction between these components. Thus, for example, activation of the catalytic activity of PKR protein kinase in response to a test agent would demonstrate the ability of that agent to interfere with NS5A's inhibition of PKR.

The screening can be performed by adding the test agent to intact cells which have been infected by virus and then examining the component of interest by whatever procedure has been established to demonstrate the viral effect on this component. Alternatively, the screening can be performed by adding the test agent to in vitro translation reactions and then proceeding with the established analysis. As another alternative, purified or partially purified components which have been determined to interact with one another by the methods described above can be placed under conditions in which the interaction between them would normally occur, with and without the addition of the test agent, and the procedures previously established to analyze the interaction can be used to assess the impact of the test agent. In this approach, the purified or partially purified components may be prepared by fractionation of extracts from uninfected and infected cells, or they may be obtained by expression of cloned genes or cDNAs or fragments thereof, optionally followed by purification of the expressed material.

Within the broad category of in vitro selection methods, several types of method are likely to be particularly convenient and/or useful for screening test agents. These include but are not limited to methods which measure a binding interaction between two or more components, methods which measure the activity of an enzyme which is one of the interacting components, and methods which measure the activity or expression of "reporter" protein, that is, an enzyme or other detectable or selectable protein, which has been placed under the control of one of the components.

Binding interactions between two or more components can be measured in a variety of ways. One approach is to label one of the components with an easily detectable label, place it together with the other component(s) in conditions under which they would normally interact, perform a separation step which separates bound labeled component from unbound labeled component, and then measure the amount of bound component. The effect of a test agent included in the binding reaction can be determined by comparing the amount of labeled component which binds in the presence of this agent to the amount which binds in its absence.

The separation step in this type of procedure can be accomplished in various ways. In one approach, (one of) the binding partner(s) for the labeled component can be immobilized on a solid phase prior to the binding reaction, and unbound labeled component can be removed after the binding reaction by washing the solid phase. Attachment of the binding partner to the solid phase can be accomplished in various ways known to those skilled in the art, including but not limited to chemical cross-linking, non-specific adhesion to a plastic surface, interaction with an antibody attached to the solid phase, interaction between a ligand attached to the binding partner (such as biotin) and a ligand-binding protein (such as avidin or streptavidin) attached to the solid phase, and so on.

Alternatively, the separation step can be accomplished after the labeled component had been allowed to interact with its binding partner(s) in solution. If the size differences between the labeled component and its binding partner(s) permit such a separation, the separation can be achieved by passing the products of the binding reaction through an ultrafilter whose pores allow passage of unbound labeled component but not of its binding partner(s) or of labeled component bound to its partner(s). Separation can also be achieved using any reagent capable of capturing a binding partner of the labeled component from solution, such as an antibody against the binding partner, a ligand-binding protein which can interact with a ligand previously attached to the binding partner, and so on.

Test methods which rely on measurements of enzyme activity are performed in accordance with the characteristics of the enzyme in each case. As noted above, a variety of enzyme activities can be determined to be involved in the translational effect of a virus, including but not limited to kinases, phosphatases, glycosylases, deglycosylases, transferases, lipases, deoxyribonucleases, ribonucleases, proteases, synthetases, polymerases, and the like, as well as those other enzyme activities noted above. In general, measurements of enzyme activity require the ability to measure the product of the reaction in the presence of other materials, and often to distinguish or separate the product of the reaction from the substrate for the reaction. Methods which may be used to measure reaction products include but are not limited to measurement of the transfer or incorporation of a radioactive or other labeled atom or group, spectrophotometric or colorimetric measurement of the concentration of the product, measurement of light output from a luminescent or chemiluminescent reaction, measurement of fluorescence from a fluorescent product, immunoassays, other immunochemical procedures, and other competitive binding assays. Enzyme activity can also be measured using any of the procedures just mentioned to detect the product of a secondary reaction or reactions which rely on the product of the reaction of interest as a substrate or a cofactor.

In many cases the product of an enzyme reaction can be detected without separating that product from other constituents of the reaction mixture, as for example when an uncolored chromogenic substrate gives rise to a colored product or the absorption spectrum for the product is different from that of the substrate, allowing selection of a wavelength for absorbance measurements of just the product. Immunoassays, other immunochemical procedures and other competitive binding assays can also often be performed without first separating the product of interest.

In other cases it may be necessary to include a separation step or steps to separate the product from other constituents of the reaction mixture before measuring it. In such cases, the necessary separation can be accomplished by a variety of procedures, including but not limited to centrifugation, trichloroacetic acid precipitation, ethanol precipitation, ammonium sulfate precipitation, filter binding, other differential precipitations, gel filtration, ion exchange chromatography, hydrophobic interaction chromatography, reverse phase chromatography, affinity chromatography, differential extractions, isoelectric focusing, electrophoresis, isotachophoresis, and the like.

In addition to methods which measure the activity of an enzyme implicated in a viral effect on translation, test methods may also be employed which have been configured such that the component(s) implicated in the viral effect controls the activity or expression of a "reporter" protein, that is, an enzyme or other detectable or selectable protein. In the case, for example, where a kinase has been implicated in the viral effect, the test method might be configured in such a way that phosphorylation of a particular protein by the kinase leads to the activation or inhibition of that protein or of some other protein controlled by that protein. In yeast, for example, phosphorylation of eIF2-α by the GCN2 protein (or by mammalian PKR kinase substituting for GCN2) leads to an inhibition of the initiation of translation, which in turn leads to an increase in the synthesis of the GCN4 protein, which in turn induces the synthesis of further proteins involved in amino acid biosynthesis. "Reporter" proteins can be readily fused to the GCN4 protein at the genetic level so that the synthesis of these reporters is effectively induced by the initial phosphorylation event catalyzed by GCN2 or mammalian PKR.

Similar approaches can be used to detect modulation by test agents of the activity of a variety of other components which might be implicated in viral effects on translation. The effect of a test agent on a protease, for example, can be monitored by following the survival in an in vitro reaction of a reporter protein which is a target for that protease. Similarly, the effect of a test agent on a nuclease can be monitored by following the appearance in an in vitro translation reaction or in vitro transcription-translation reaction of a reporter protein translated from a suitably configured coding sequence provided to the reaction.

Proteins suitable for use as reporters in such assays include, but are not limited to, easily assayed enzymes such as β-galactosidase, luciferase, β-glucuronidase, chloramphenicol acetyl transferase, and secreted embryonic alkaline phosphatase; proteins for which immunoassays are readily available such as hormones and cytokines; proteins which confer a selective growth advantage on cells such as adenosine deaminase, amino-glycoside phosphotransferase (the product of the neo gene), dihydrofolate reductase, hygromycin-B phosphotransferase, thymidine kinase (when used with HAT medium), xanthine-guanine phosphoribosyltransferase (XGPRT), and proteins which provide a biosynthetic capability missing from an auxotroph; proteins which confer a growth disadvantage on cells, for example enzymes that convert non-toxic substrates to toxic products such as thymidine kinase (when used with medium containing bromodeoxyuridine) and orotidine-5'-phosphate decarboxylase (when used with 5-fluoroorotic acid); and proteins which are toxic such as ricin, cholera toxin or diphtheria toxin.

Many of the methods so far described for selecting test agents have involved examining the impact of these agents on the interaction between two or more components in vitro reactions. The interacting components can also be brought into contact with one another within cells rather than in vitro reactions. In this approach, coding sequence(s) encoding part or all of a component or components would be introduced into a selected type of cell. Coding sequences for this approach include cloned genes or cDNAs or fragments of either or fragments amplified by the polymerase chain reaction or natural RNAs or transcribed RNAs or the like. Several variations of the approach are possible. In one variation, a coding sequence is introduced for a first component into a cell known to contain components with which this first component will interact. Thus, for example, a coding sequence for a viral component is introduced into a cell which is a normal target for infection by the virus in question. Agents are tested to select those which block the effect of the viral component within the cell into which the coding sequence has been introduced. In another variation, coding sequences for two or more component which interact with one another might be introduced into a cell, and agents tested for their ability to moderate the interaction between these components, this interaction being followed by the procedures previously established as suitable for the purpose. The cell into which the coding sequences are introduced can be one which would normally be a target for infection by the virus in question. Alternatively and usefully, the cell can be one which is easier to grow, manipulate and test such as a yeast cell. Indeed, there are distinct advantages to reconstructing a translation control mechanism in heterologous cells, in which the interactions between the components involved are easier to study than they are when those components are in their normal environment. In the case of yeast, in particular, the powerful genetic approaches available often make it possible to identify and isolate the yeast homologues of genes from higher eukaryotes more quickly than the corresponding genes can be identified in the higher eukaryotes.

From the foregoing it should be apparent that one skilled in the art is able to choose from a wide variety of methods at each stage in the identification of components involved in viral effects on translation, in the characterization of the interaction between these components, and in the implementation of screening tests to select compounds which moderate or abolish the interaction between these components.

The following is a more detailed outline of the specific screening and related protocols useful in this invention. A method for screening agents effective to interfere with viral proteins expressing an ISDR inhibition of PKR protein kinase is described. As one detailed example, the system chosen is one in which the virus is able to produce a viral inhibitor which interferes with the activity of the host-cell interferon-induced, double-stranded RNA-activated protein kinase. As noted above, however, this example is not limiting in the invention and only exemplifies the broad scope of the invention.

The method generally includes the steps of incubating the protein kinase, the viral inhibitor, and the compound to be tested, under conditions effective to cause viral inhibitor interference with the activation of the protein kinase, and examining the mixture for interference. The invention contemplates four general embodiments, as detailed below.

5.4.1 In Vitro Screening Assays

In one example, the method is used for screening a compound effective to inhibit replication in a host cell of a virus which produces a viral inhibitor able to bind to the PKR protein kinase and block its activation by double-stranded RNA (dsRNA). Here, the incubating step includes incubating the mixture under conditions effective to bind the viral inhibitor to the protein kinase, and the examining step includes examining the protein kinase for bound viral inhibitor.

The incubating may be carried out, for example, in solution phase, and the examining step includes passing the mixture through a filter which retains the viral inhibitor only when the inhibitor is bound to the protein kinase.

Alternatively, the protein kinase may be bound to a solid support, the viral inhibitor labeled with a reporter, and the examining step performed by measuring the amount of reporter bound to the solid support.

Alternatively, the incubating may be carried out under conditions in which the protein kinase is autophosphorylated, in the absence of binding to the viral inhibitor, and the examining step performed by determining the extent of phosphorylation of the PKR kinase.

In a second example, the incubating step includes incubating the mixture under conditions effective for the PKR kinase to be activated in the absence of the viral inhibitor, and the examining step includes examining the activity of the PKR kinase in the presence of the inhibitor.

The incubating may be carried out, for example, using a purified or partially purified PKR kinase preparation, and the examining step includes measuring autophosphorylation of the kinase or phosphorylation of eIF2-alpha or histone substrates provided to the kinase.

Alternatively, the incubating may be carried out in an in vitro translation mixture containing the PKR kinase, and the examining step includes measuring the amount of a reporter polypeptide produced by translation of specific mRNA. The mRNA may be one whose translation is reduced by activation of PKR kinase, or preferably, one whose translation is increased, such as a chimeric RNA whose 5'-untranslated leader is derived from the yeast GCN4 gene.

In a third example, the method is used for screening compounds effective in blocking viral replication of a virus which produces a viral inhibitor effective to activate a host-cell component which is able in activated form to block activation of the protein kinase or inhibit the activated kinase. Here the mixture formed includes the host-cell component (in activated form), the incubating step is carried out under conditions in which the protein kinase is activated, in the absence of the activated component, and the examining step includes examining the mixture for inhibition of protein kinase activity. Alternatively, the mixture formed includes the host-cell component in non-activated form and the viral inhibitor which activates the host-cell component, the incubating step is carried out under conditions in which the protein kinase is activated, in the absence of the viral inhibitor and activated host-cell component, and the examining step includes examining the mixture for inhibition of protein kinase activity.

5.4.2 In Vivo Screening Assays

The present invention also relates to in vivo screening assays to identify compounds effective to inhibit viral replication in a host cell. For these assays, host cells to which the test compound is added may be genetically engineered to express both NS5A and PKR or fragments thereof as described in Section 5.2. The expression of NS5A and PKR in the host cells may be transient, induced or constitutive, or stable. The ability of a test compound to interfere with NS5A/PKR interactions can be measured by adding the test compound to the host cell and measuring PKR activity directly, i.e., by PKR kinase assays of a known substrate; or indirectly, i.e., by co-transfecting a reporter gene whose expression is dependent on the presence of activated PKR kinase. For the purposes of the screening methods of the present invention, a wide variety of host cells may be used including, but not limited to, tissue culture cells, mammalian cells, yeast cells, and bacteria. Each cell type has its own set of advantages and drawbacks. Mammalian cells, such as cultured liver cells may be a preferred cell type in which to carry out the assays of the present invention, however these cell types are sometimes difficult to cultivate. Bacteria and yeast are relatively easy to cultivate but process proteins differently than mammalian cells. The in vivo screening method will be illustrated by reference to a yeast host cell expression system, but the principles of the approach can be applied to any genetically engineered host cell as described in Section 5.2 infra.

In an illustrative embodiment of the invention, the viral or virus-activated inhibitor is expressed in a yeast cell which is constructed to increase the expression of a reporter polypeptide in the presence of activated PKR kinase, and the examining step includes examining the yeast cells for increased expression of the reporter polypeptide.

One of the yeast proteins which participates in translation control is the protein GCN2. The protein is a kinase which is activated by binding of uncharged tRNAs, which accumulate when amino acids are in short supply. The activated protein inhibits translation levels in yeast, by phosphorylating the alpha subunit of the initiation factor eIF2. Another result of GCN2 activation is increased production of a yeast GCN4 protein, which then activates anabolic pathways for the synthesis amino acids.

A construct used in the present invention for in vivo screening is a yeast cell in which the GCN2 gene is replaced with a mammalian PKR gene under the control of a regulated promoter. The cell also includes the additional modifications described below. Introduction of the PKR gene into yeast can be carried out using standard recombinant techniques for introducing a selected coding sequence into yeast. Briefly, the PKR gene is placed under the control of a down-regulatable promoter, with cell selection occurring under down-regulated conditions. This is done because in yeast cells the PKR protein is constitutively activated, presumably by endogenous dsRNA, and if expressed at too high a level it inhibits cell translation in its activated condition.

The yeast cells are then further constructed to enable the regulation of PKR to be tested by examining the levels of a reporter polypeptide whose production is dependent on the presence of activated PKR enzyme. Such a reporter can be produced from a β-gal gene fused to the GCN4 yeast gene. The latter gene becomes expressed under conditions of GCN2 activation, and has been shown to be under the control of the PKR phosphorylation system in yeast cells in which GCN2 has been replaced with PKR. Thus, the presence of activated PKR leads to a shutdown of yeast translation in general, but to enhanced production of the fused GCN4/β-gal protein. The expression of the fused protein can be measured easily by measuring β-gal activity.

The screening system is designed for screening drugs which are effective to disrupt a viral pathogen's counter-defense against the host cell's attempt to shut down cell translation, by activation of the PKR protein. The viral counter-defense may include, among others, (a) a VA1, EBER-1, or TAR viral inhibitor RNA which occupies the binding site on PKR and prevents dsRNA from binding to and activating PKR, or (b) the ability of the virus, e.g., influenza virus, to induce or activate a cellular component which is effective to prevent activation of PKR or deactivate the activated enzyme, or (c) a viral protein such as reovirus σ3 protein or vaccinia virus K3L and E3L proteins which blocks the activation or activity of PKR, or (d) a complex of a cellular component with a viral RNA, such as the complex used by poliovirus to degrade the PKR kinase.

In the case of a viral inhibitor, the yeast cells used in screening are further constructed to contain the gene for the viral inhibitor under the control of an inducible promoter. Under non-inducing growth conditions, in which the viral inhibitor is not expressed (but PKR protein is), the PKR protein is activated, presumably by endogenous dsRNA as noted above, and the presence of activated PKR is manifested by relatively high measured levels of the GCN4/β-gal fusion protein. Under inducing growth conditions, for example, when the growth medium includes the inducer for the inducible promoter which controls the expression of the viral inhibitor, the cells show low levels of activated PKR due to the presence of the viral inhibitor, and this is manifested by relatively low levels of the GCN4/β-gal fusion protein. Potential antiviral agents are tested by assessing their impact on the measured levels of the GCN4/β-gal fusion protein under inducing conditions for the viral inhibitor. Those agents which allow relatively high levels of fusion protein to be synthesized are selected, as being agents which prevent the viral inhibitor from interfering in activation of PKR by endogenous double-stranded RNA.

In the case of a cellular component induced or activated by a virus to prevent activation of PKR kinase or inhibit activated kinase, the gene for this cellular component is placed in the yeast cells used for screening under the control of an inducible promoter (in place of the viral inhibitor RNA gene described above). The yeast strain is then used for screening essentially as described for viral inhibitors. Thus, under non-inducing growth conditions the cellular component is not expressed, and relatively high levels of the GCN4/β-gal fusion protein are observed, reflecting the presence of PKR activated by endogenous double-stranded RNA. Under inducing growth conditions, the levels of the GCN4/β-gal fusion protein are lower, reflecting inhibition of the activation or activity of PKR by the cellular component. Potential antiviral agents are tested by assessing their impact on the measured levels of the GCN4/β-gal fusion protein under inducing conditions for the cellular component, and agents selected which allow relatively high levels of fusion protein to be synthesized.

A similar approach is adopted in the case of a complex between a cellular component and a viral component which degrade the PKR kinase. In this case, the yeast strain would be further constructed to contain genes for both the cellular and the viral component under inducible control, and the screening would be performed essentially as described above. The following examples illustrate the screening methods described above, but in no way are intended to limit the scope of the invention.

5.5 Targeting NS5A in the Reatment of HCV

A variety of techniques and compositions may be utilized to target NS5A to inhibit its activity or to inhibit the interaction between NS5A and IFN-induced proteins, thereby inhibiting HCV infection.

For example, compounds which may be used in accordance with the present invention encompass any compound which targets NS5A to inhibit its activity or interferes with the interaction between NS5A and IFN-induced PKR, including but not limited to neutralizing antibodies against NS5A or the ISDR. Other examples of compounds include but are not limited to peptides (such as, for example, peptides representing those regions of NS5A required for its interaction with IFN-induced PKR, such as the ISDR), phosphopeptides, small organic or inorganic molecules, or antibodies (including, for example, Epolyclonal, monoclonal, humanized, anti-idiotypic, chimeric or single chain antibodies, and FAb, F(ab')$_2$ and FAb expression library fragments, and epitope-binding fragments thereof). Techniques for determination of effective doses and administration of such compounds are described below, in Section 5.6 infra.

In addition, compounds which may also be used in accordance with the present invention, include intracellular drugs that inhibit NS5A activity—competing ligands that prevent IFN-induced PKR from interacting with NS5A.

Gene therapy approaches may also be used in accordance with the present invention to inhibit the interaction of NS5A and IFN-induced proteins. Among the compounds which may disrupt the interaction of NS5A, and in particular the ISDR with its cellular targets are antisense, ribozyme and triple helix molecules. Such molecules are designed to inhibit the expression of the target gene, NS5A, in HCV-infected host cells. Techniques for the production and use of antisense ribozyme and/or triple helix molecules are well known to those of skill in the art and can be designed with respect to the nucleotide sequence encoding the amino acid sequence of ISDR as shown in FIG. 1A.

Antisense RNA and DNA molecules act to directly block the translation of mRNA by hybridizing to targeted mRNA and preventing protein translation. With respect to antisense DNA, oligodeoxynucleotides derived from the translation initiation site, e.g., between the −10 and +10 regions of the target gene nucleotide sequence of interest, are preferred.

Ribozymes are enzymatic RNA molecules capable of catalyzing the specific cleavage of RNA. (For a review see Rossi, J., 1994, Current Biology 4:469–471). The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence see U.S. Pat. No. 5,093,246, which is incorporated by reference in its entirety. As such, within the scope of the invention are engineered hammerhead motif ribozyme molecules that specifically and efficiently catalyze endonucleolytic cleavage of RNA sequences encoding target gene proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridize with complementary oligonucleotides, using ribonuclease protection assays.

Nucleic acid molecules to be used in triple helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'–3', 3'–5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may be introduced into cells via gene therapy methods such as those described, that do not contain sequences susceptible to whatever antisense, ribozyme, or triple helix treatments are being utilized. Alternatively, in instances whereby the target gene encodes an extracellular protein, it may be preferable to coadminister normal target gene protein in order to maintain the requisite level of target gene activity.

Anti-sense RNA and DNA, ribozyme, and triple helix molecules of the invention may be prepared by any method known in the art for the synthesis of DNA and RNA molecules. These include techniques for chemically synthesizing oligodeoxyri-bonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include but are not limited to, the addition of flanking sequences of ribo- or deoxy-nucleotides to the 5' and/or 3' ends of the molecule or the use of phosphorothioate or 2' o-methyl rather than phosphodiesterase linkages within the oligodeoxyribonucleotide backbone.

5.6 Pharmaceutical Formulations and Methods of Administration

The present invention encompasses the novel antiviral agents identified by the screening methods of the invention in pharmaceutical compositions and therapeutic modalities for the treatment of viral infections using ISDR containing proteins as the target for intervention. In one embodiment of the present invention, the novel antiviral agents identified by the screening assays of the present invention may be used in combination with other known antiviral agents to treat viral infections.

5.6.1 Antivirals to be Used in Combination With a NS5A Inhibititor

According to the present invention, novel antiviral agents identified by the screening methods of the present invention may be used in combination with other therapeutic agents to enhance the antiviral effect achieved. Preferably a NS5A inhibitor is used in combination with another antiviral agent. In another embodiment of the present invention an agent which induces IFN-expression to a level that results in override of NS5A inhibition of PKR may be used in combination with another antiviral agent. Such additional antiviral agents which may be used with a NS5A inhibitor include, but are not limited to, those which function on a different target molecule involved in viral replication, e.g., inhibitors of preferential translation; those which act on a different target molecule involved in viral transmission; those which act on a different loci of the same molecule; and those which prevent or reduce the occurrence of viral resistance. one skilled in the art would know of a wide variety of antiviral therapies which exhibit the above modes of activity.

In one embodiment of the invention, novel antiviral agents identified by the screening methods of the present invention are used in combination with IFN therapies. The antiviral agents identified by the screening methods of the present invention may also be used in combination with exogenous or endogenous agents which induce IFN expression. In yet another embodiment, inhibitors of NS5A are used in combination with inhibitors of preferential translation in order to target two different molecules required in the viral life cycle.

In order to evaluate potential therapeutic efficacy of NS5A inhibitors in combination with the antiviral therapeutics described above, these combinations may be tested for antiviral activity according to methods known in the art.

A compound of the invention can be administered to a human patient by itself or in pharmaceutical compositions where it is mixed with suitable carriers or excipients at doses to treat or ameliorate various conditions involving HCV-infection. A therapeutically effective dose further refers to that amount of the compound sufficient to inhibit HCV infection. Therapeutically effective doses may be administered alone or as adjunctive therapy in combination with other treatments for HCV infection or associated diseases. Techniques for the formulation and administration of the compounds of the instant application may be found in "Remington's Pharmaceutical Sciences" Mack Publishing Co., Easton, Pa., latest addition.

5.6.2 Routes of Administration

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation.

Furthermore, one may administer the agent of the present invention in a targeted drug delivery system, for example in a liposome targeted to the liver. The liposomes will be targeted to and taken up selectively by liver cells.

5.6.3 Composition/Formulation

The pharmaceutical compositions of the present invention may be manufactured in a manner that is itself known, e.g., by means of conventional mixing, dissolving, dragee-making, levitating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers, such as Hank's solution, Ringer's solution, or physiological saline buffer. For transmucosal administration, penetrants appropriate to the barrier to be permeated are used in the formulation. Such penetrants are usually known in the art.

For oral administration, the compounds can be formulated readily by combining the active compounds with pharmaceutically acceptable carriers well known to those in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for infection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention identified as inhibitors of the interaction between NS5A and IFN-induced PKR may be provided as salts with pharmaceutically compatible counterions. Pharmaceutically compatible salts may be formed with many acids, including but not limited to hydrochloric, sulfuric, acetic, lactic, tartaric, malic, succinic, etc.; or bases. Salts tend to be more soluble in aqueous or other protonic solvents that are the corresponding free base forms. Examples of pharmaceutically acceptable salts, carriers or excipients are well known to those skilled in the art and can be found, for example, in Remington's Pharmaceutical Sciences, 18th Edition, A. R. Gennaro, Ed., Mack Publishing Co., Easton, Pa., 1990. Such salts include, but are not limited to, sodium, potassium, lithium, calcium, magnesium, iron, zinc, hydrochloride, hydrobromide, hydroiodide, acetate, citrate, tartrate, malate sales, and the like.

5.6.4 Effective Dosage

Pharmaceutical compositions suitable for use in the present invention include compositions wherein the active ingredients are contained in an effective amount to achieve their intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. Such information can be used to more accurately determine useful doses in humans.

A therapeutically effective dose refers to that amount of the compound that results in a reduction in the intensity of the infection or in amelioration of symptoms or a prolongation of survival in a patient. Toxicity and therapeutic efficacy of such compounds can be determined by standard pharmaceutical, pharmacological, and toxicological procedures in cell cultures or experimental animals, eg., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from cell culture assays or animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p. 1).

Dosage amount and interval may be adjusted individually to provide plasma levels of the active moiety which are sufficient to maintain the desired modulating effects, or minimal effective concentration (MEC). The MEC will vary for each compound but can be estimated from in vitro data; e.g., the concentration necessary to achieve a 50–90% inhibition of HCV infection using the assays described herein. Dosages necessary to achieve the MEC will depend on individual characteristics and route of administration. However, HPLC assays, bioassays or immunoassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

In immunization procedures, the amount of immunogen to be used and the immunization schedule will be determined by a physician skilled in the art and will be administered by reference to the immune response and antibody titers of the subject.

5.6.5 Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

6. EXAMPLE: NS5A and PKR Interact in Vitro

The following in vitro experiments demonstrate that the HCV protein NS5A associates with interferon-induced PKR in vitro and were carried out to test the hypothesis that HCV NS5A directly represses the activity of PKR through a physical interaction with the kinase.

6.1. Materials and Methods

Plasmid construction: To generate wild type HCV laNS5A constructs, the complete NS5A coding region from pSPns % (HCV-1a) was amplified by PCR using the oligonucleotide primers A, 5'-GGAATTCGAGCTCGCCCG and B, 5-'GCTCTAGAAGCACACGACATCTTC (EcoRI and XbaI sites underlined). The resulting product was directly cloned into pCR2.1 (Invitrogen) to yield plasmid pNS5A/CR2.1. The NS5A coding region was removed from pNS5A/CR2.1 as an EcoRI fragment for insertion in pBD (Strategene) to yield pBD-NS5A, or as an EcoRI-XbaI fragment for insertion into pcDNA3.1/His and pYES2 (Invitrogen), to give pcDNA3.1/His-NS5A and pYES2-NS5A, respectively. To generate the ISDR deletion mutant of NS5A, individual N-terminal and C-terminal coding fragments, each of which lacked the ISDR were generated. The N-terminal region, encoding amino acids 1–236, was amplified by PCR using primer A and primer C, 5'-CCACTCGAGCGGACAGTTGGCTGG (XhoI site underlined). The C-terminal region, encoding amino acids 278–447, was amplified using primer B and primer D, 5'-CCGCTCGAGTGGTGATTCTGGTCTC (XhoI site underlined). The resulting PCR products were cloned directly into pCR2.1 to yield pN/CR2.1 and pC/CR2.1, respectively. The N-terminal coding region of NS5A was then removed from pN/CR2.1 for insertion into pcDNA-3, 1/His to generate pcDNA3.1/His-NS5A 1–236. An ISDR deletion construct was prepared by insertion of the C-terminal coding fragment into the XhoI and XbaI sites of pcDNA3.1/His-NS5A 1–236 fused in-frame with amino acids 278–447, deleting the entire ISDR. The insert from pcDNA3.1/His-ΔISDR was then subcloned into the 2μ yeast expression vectors pBD and pYES2 to give pBD-ΔISDR and pYES2-ΔISDR, respectively. To obtain the NS5A coding region from HCV-1b, viral RNA was extracted from 100 μl of serum (Chomczynski and Sacchi, 1987, Anal. Biochem. 162:156–159) obtained under informed consent from a genotype 1b patient who failed to respond to IFN therapy. Response to IFN was determined by RT-PCR and bDNA assay, as previously described (Gretch et al., 1993, J. Clin. Micro. 31:289–291). Verification of HCV genotype was determined by a combination of RFLP and genotype-specific PCR analyses of the viral 5' untranslated region and sequences encoding the core protein, respectively (Davidson el al., 1995, J. Gen. Virol. 76:1197–1204; Okamoto et al., 1992, J. Gen. Virol. 73:673–679). Viral cDNA was synthesized by reverse transcription using the priming oligonucleotide 5'GTGGTGACGCAGCAGAGAGT (corresponding to nt 7681–7700 of HCV-J (Bukh el al., 1995, Semin. Liver Dis. 15:41–63), followed with first-round PCR by the addition of the upstream primer 5'CAGCCTCACCATCACT-CAGC (corresponding to HCV-J nt 6256–6275). For directional cloning of NS5A, first-round PCR products were further amplified using the NS5A-specific nested-set oligonucleotide primer pair 5'CCTTCCATGGGCTCCG-GCTCGTGGCTAAAG and 5'ATCGGATCCTTAGGA-CATTGAGCAGCAGACGA (Nco1 and BamH1 sites underlined, respectively). After restriction enzyme digestion, the purified PCR products were cloned into the corresponding sites of pACT2 (Clontech) to give pAD-NS5A which encodes an AD-NS5A fusion protein corresponding to HCV-1b. While the relationship between the ISDR aa sequence of HCV-1a and IFN sensitivity has not been precisely determined, this region of NS5A (aa 237–276) possessed significant aa identity to the prototypic IFN-resistant ISDR sequence defined previously (Enomoto el al., 1996, N. Engl. J. Med. 334:77–81; Enomoto et al., 1995, J. Clin. Invest. 96:224–230) and present in our HCV-Ib NS5A clone (FIG. 1A). Construction of PKR plasmids PBD-PKR K296R, pAD-PKR aa constructs K296R, 1–242, 244–551, 244–366, 367–551 and pAD-P58$^{IPK}$ wt were described previously (Gale, Jr. et al., 1996, Mol. Cell. Biol. 16:4172–4181). pBD-PKR 99–551 was constructed by recovering the 1.6 kb Nde1/BamH1 fragment from pET11A-PKR M7 (Barber et al., 1995, Mol. Cell. Biol. 15:3188–3146) and cloning it into the corresponding sites of pGBT10 (Gale, Jr. et al., 1996, Mol. Cell. Biol. 16:4172–4181) pEMBLYex4-K3L contains the entire vaccinia virus X3L gene inserted into pEMBLYex4 and is described in a separate manuscript. GST-NS5A was produced by introducing the BamHl fragment from the HCV-1a NS5 clone pSPns5 into the plasmid pGEX2T (Smith and Johnson, 1988, Gene 67:31–40) to give pGST-NS5A. This construct encodes NS5A aa 1–427 fused in frame with the glutathione-S-transferase protein. The nt sequences of all constructs used in this study were confirmed by double stranded DNA sequence analysis using an Applied Biosystems automated sequencer.

Analysis of protein interaction in vitro: E. coli harboring pGEX2T or pGST-NS5A were grown in liquid culture and GST or GST-NS5A expression induced by the addition of isopropyl thiogalactopryanoside into the culture medium. Bacteria were harvested and extracts prepared for binding analyses as described previously (Gale, Jr. et al., 1996, Mol. Cell. Biol. 16:4172–4181). For binding analyses, expression of GSTr or GST-NS5A was confirmed in recombinant extracts by immunoblot analysis using either a GST-specific antiserum or an antiserum specific to a superoxide dismutatse-NS5 fusion protein (anti-NS5; Chiron Corporation). Positive recombinant extracts were used for in vitro binding analysis. Wt human PKR and PKR deletion mutants were in vitro transcribed from the T7 promoter of pcDNA1neo and translated in the presence of [$^{35}$S]-methionine as described previously (Katze et al., 1991, Mol. Cell. Biol. 11:5497–5505). For in vitro binding analyses, approximately $1 \times 10^5$ counts of trichloroacetic acid. precipitable-material from each translation reaction were added to a crude E. coli extract containing either GST or GST-NS5A and processed as described (Gale, Jr. el al., 1996, Mol. Cell. Biol. 16:4172–4181). Labeled proteins which bound to GST or GST-NS5A were separated by SDS-PAGE and visualized by autoradiography of the dried gel.

In vitro assay of PKR function: For PKR in vitro kinase assays and GSTNS5A were purified from E. coli extracts using glutathione-agarose affinity chromatography. Native PKR was affinity purified from IFN-treated human 293 cells (Galabru and Hovanessian, 1987, J. Biol. Chem. 262:15538–15544). The concentration of all purified proteins was assessed by quantitative SDS-PAGE using BSA as a standard. In vitro kinase assays were carried out essentially as described (Tang et al. 1996, J. Biol. Chem., except that PKR was preincubated with increasing concentrations of GST or GST-NS5A prior to the addition of histone substrates and [$^{32}$P]-γATP. Kinase reaction products were separated by SDS-PAGE and the dried gel subjected to autoradiography for visualization of phosphorylated substrates. It was shown previously that there is a perfect correlation between phosphorylation of histones and purified eIF-2α by PKR in vitro (Katze et al. 1991, Mol. Cell. Biol. 11:5497–5505).

6.2. Results

NS5A o'btained from HCV 1-a (FIG. 1) was used to test the ability of NS5A to directly interact with PKR. NS5A expressed as a glutathione-S-transferase (GST) fusion protein in E. coli (GST-NS5A) specifically interacted with in vitro translated full length PKR using a GST-pull down assay. As seen in FIG. 2, PKR aa 244–551 were both necessary and sufficient for complex formation with GST-NS5A. Thus, recombinant NS5A can specifically form a complex with PKR in vitro which maps to within the protein kinase catalytic domain-inclusive PKR C-terminus.

7. Example
NS5A INTERACTS WITH THE PXR KINASE CATALYTIC DOMAIN IN VIVO

The following experiments were carried out to determine the interaction between NS5A and PKR in vivo.

7.1. Materials and Methods

Analysis of protein interaction in vivo: For analysis of protein interactions the Saccharomyces cerevisiae strain Hf7c (MATa ura 3-52 his 3-200 lys2-801 ade2-101 trp 1-901 lea2-3, 112 gal4-542 gal80-538 LYS2::GAL1-HIS3 URA3:: (GAL4 17-mers)$_3$-cycl-lacZ) were employed in a two-hybrid assay (Fields and Song, 1989, Nature 340:245–246). For the two-hybrid assay and the yeast assays described below, cells were transfected by the lithium acetate method with the indicated expression constructs. For 2-hybrid analysis, it was first verified expression of all AD- and BD-fusion proteins in the transfected yeast clones by immunoblot analysis, using anti-AD or anti-BD monoclonal antibodies (Clontech) as described by the manufacturer. In yeast strain Hf7c, synthesis of histidine is dependent upon interaction of the 2-hybrid proteins. Thus, in the presence of a 2-hybrid protein interaction strains will exhibit growth on histidine deficient medium. The synthesis of the HIS reporter protein was used to assay for 2-hybrid protein interaction, as recently described (Gale, Jr. et al., 1996 supra). Initial transfectants were selected on SD medium lacking the aa Trp and Leu (+His medium). Transfectants were subsequently streaked onto SD medium lacking the aa His, Trp and Leu (−His medium) and were grown for 3–6 days to allow depletion of residual histidine stores. Colonies were restreaked onto −His medium and scored for growth after 3–7 days. The induction of reporter gene expression in our 2-hybrid yeast clones was confirmed by measuring LacZ expression using a liquid assay and the fluorogenic substrate 4-methylumbelliferyl-β-D-galactoside (MUG) as described (Cao and Geballe, 1994, Virology 205:151–160,).

Yeast growth repression assay for determination of NS5A and PKR function in vivo: For determination of NS5A and PKR function in vivo Saccharomyces cerevisiae strain RY1-1 (MATa ura3-52 leu2-3 leu2-112 gcn2Δ trp1-Δ63 LEU2:: (GAL-CYC1-PKR)$_2$ which carries 2 copies of human PKR integrated into the LEU2 locus was utilized, under control of the galactose inducible GAL1-CYC1 promoter (Romano et al., 1995, Mol. Cell. Biol. 15:365–378). When grown on inducing medium, this strain exhibits a slow growth phenotype due to the PKR-mediate phosphorylation of yeast eIF-2α. Protein expression was verified by immunoblot analysis using either an anti-PKR mab (Laurent et al., 1985, Proc. Natl. Acad. Sci. USA 82:4341–4345) or antisera generated against a recombinant NS5 protein (α-NS5). Both NS5A and ΔISDR constructs were efficiently expressed from the pyes plasmid. In addition, it was found that coexpression of NS5A or ΔISDR had no effect on PKR levels which were expressed efficiently to equal levels in both transfected strains. To assess growth of RY1-1 transfectants, yeast colonies were streaked onto uracil deficient SD medium and SGAL medium as described by Romano et al. (Romano et al., 1995 supra). Growth was assessed at 3–7 days post-streaking of colonies.

7.2. Results

To confirm and extend these results, NS5A-PKR interaction studies were carried out using the yeast 2-hybrid system, scoring for growth on histidine deficient medium as a positive 2-hybrid protein interaction. For comparison an assessment of the P58$^{IPK}$-PKR interaction described previously was included (Gale, Jr. et al., 1996 supra). It was found that full length NS5A from an IFN-resistant isolate of strain HCV-1b fused to the GAL4 activation domain (AD-NS5A), specifically interacted with the inactive full length PKR mutant, PKR K296R and the truncated mutant PKR 98–551, each fused to the GAL4 DNA binding domain (BD) (FIG. 2). BD-PKR 98–551 lacks the first dsRNA binding domain (FIG. 1B) and is deficient in binding dsRNA (Barber et al., 1995, Mol. Cell. Biol. 15:3138–3146). Thus, similar to the cellular PKR inhibitor, P$_{58}$$^{IPK}$, HCV-1b NS5A can physically interact with PKR. Furthermore, these results indicate that the NS5A-PKR interaction is not a dsRNA-mediated event.

The ability of BD-NS5A, from an HCV-1A isolate, to interact with AD-PKR in vivo using the 2 hybrid assay. As seen in FIG. 4, BD-NS5A from HCV 1a specifically interacted with AD-PKR K296R in yeast cotransfectants, as determined by growth in −His medium. Thus, NS5A from the independent strains HCV-1a and HCV-1b, can physically interact with PKR in vivo. To map the NS5A-interactive region of PKR, a series of AD-PKR mutants to transfect yeast harboring the HCV 1a BD-NS5A construct were employed. BD-NS5A specifically interacted with the PKR catalytic domain, mapping to within PKR aa 244–366, as AD-constructs PKR 244–551 and PKR 244–366 both mediated growth on −His medium (FIG. 4). The NS5A-interactive region of PKR was exclusive of both the C-terminal 184aa and the N-terminal 242aa, as yeast cotransfectants harboring AD-PKR 367–551 and AD-PKR 1–242 failed to grow on −His medium. These results indicate that HCV NS5A interacts with structures within the PKR protein kinase catalytic domain. The NS5A-interactive region of PKR (aa 244–366) includes the region that interacts with the cellular PKR inhibitor, P$_{58}$$^{IPK}$ (FIG. 1B) (Gale, Jr. et al., 1996). This region of the protein kinase catalytic domain functions cooperatively in nucleotide binding and catalysis (Hanks et al., 1988, Science 241:42–52; Bossemeyer, 1995, FEBS. Lett. 369:57–61; Taylor et al., 1993, Mol. Cell. Biol. 16:6295–6302).

8. EXAMPLE: NS5A REPRESSES PKR FUNCTION

The following experiments were carried out to determine if the NS5A-PKR interaction could result in an inhibition of PKR function.

8.1. Materials and Methods

Analysis of protein interaction in vitro: E coli harboring pGEX2T or pGST-NS5A were grown in liquid culture and GST or GST-NS5A expression induced by the addition of isopropyl thiogalactopryanoside into the culture medium. Bacteria were harvested and extracts prepared for binding analyses as described previously (Gale, Jr. et al., 1996). For binding analyses, expression of GSfr GST-NS5A was confirmed in recombinant extracts by immunoblot analysis using either a GST-specific antiserum or an antiserum specific to a superoxidedismutatse-NS5 fusion protein (anti-NS5; Chiron Corporation). Positive recombinant extracts were used for in vitro binding analysis. Wt human PKR and PKR deletion mutants were in vitro transcribed from the T7 promoter of pcDNA1neo and translated in the presence of [$^{35}$S]-methionine as described previously (Katze et al., 1991, Mol. Cell. Biol. 11:5497–5505). For in vitro binding analyses, approximately 1×10$^5$ counts of trichloroacetic acid. precipitable-material from each translation reaction were added to a crude E. coli extract containing either GST or GST-NS5A and processed as described (Gale, Jr. el al., 1996). Labeled proteins which bound to GST or GST-NS5A were separated by SDS-PAGE and visualized by autoradiography of the dried gel.

In vitro assay of PKR function: For PKR in vitro kinase assays and GSTNS5A were purified from E. coli extracts using glutathione-agarose affinity chromatography. Native PKR was affinity purified from IFN-treated human 293 cells (Galabru and Hovanessian, 1987, J. Biol. Chem. 262:15538–15544). The concentration of all purified proteins was assessed by quantitative SDS-PAGE using BSA as a standard. in vitro kinase assays were carried out essentially as described (Tang et al. 1996, J. Biol. Chem. 271:28660–28666), except that PKR was preincubated with increasing concentrations of GST or GST-NS5A prior to the addition of histone substrates and [$^{32}$P]-γATP. Kinase reaction products were separated by SDS-PAGE and the dried gel subjected to autoradiography for visualization of phosphorylated substrates. It was shown previously that there is a perfect correlation between phosphorylation of histones and purified eIF-2α by PKR in vitro (Katze et al. 1991).

8.2. Results

An in vitro analysis of PKR activity in the presence of recombinant NS5A was first carried out. Incubation of purified native PKR with recombinant GST-NS5A from HCV-1a resulted in the specific inhibition of both PKR autophosphorylation and phosphorylation of an exogenous histone substrate (FIG. 5). It is worth noting that as little as 0.2 pmol of NS5A can inhibit 1.8 pmol of PKR. At present it cannot be determined whether this results from a relatively small percentage of PKR being active or whether NS5A may function at low levels due, perhaps, to disruption of higher order PKR dimers. The loss of PKR activity was not due to degradation of PKR or NS5A-mediated hydrolysis of ATP. Furthermore, while it is possible that the inhibition of PKR and histone phosphorylation in our in vitro assay could be due to a GST-NS5A-mediated phosphatase activity, this is believed to be unlikely since NS5A does not possess any structural attributes indicative of phosphatase function. Equal molar levels of GST had no effect upon PKR activity (FIG. 5, lanes 6–9). Thus, similar to the action of other virally-encoded PKR inhibitory proteins, NS5A can specifically inhibit the function of PKR in vitro, likely through a direct effect of the NS5A-PKR interaction.

Expression of PKR in yeast provides an in vitro functional assay for direct measurement of PKR activity (Romano et al., 1995, Mol. Cell. Biol. 15:365–378). Through its eIF-2α phosphorylating activity, PKR is growth suppressive when expressed in yeast. Coexpression of PKR with transdominant inhibitory PKR mutants or virally-encoded PKR inhibitory proteins, such as HIV Tat or vaccinia virus K3L, reverses the PKR-mediated slow growth phenotype in yeast due to inhibition of PKR and a concomitant decrease in eIF-2α phosphorylation (Romano et al., 1995; McMillan et al., 1995; M. Kobayashi, E. Locke, J. Silverman. T. Ung and T. Dever, manuscript submitted). To assess the effects of NS5A on PKR function, we expressed NS5A under control of the GAL1 galactose-inducible promoter in yeast strain RY1-1, developed by Romano et al. (1995). RY1-1 possesses 2 integrated copies of human PKR under control of the GAL1-CYC1 galactose-inducible promoter and maintains a PKR-mediated growth-suppressive phenotype when grown on galactose medium. For comparison, we included a parallel analysis of RY1-1 harboring the well characterized vaccinia virus PKR inhibitor, K3L, also under control of the GAL1-CYC1 promoter (M. Kobayashi, E. Locke, J. Silverman, T. Ung and T. Dever, manuscript submitted). The examination of NS5A function began by determining the growth properties of the RY1-1 transfectants. While all transfectants maintained efficient growth on noninducing dextrose (SD) medium (FIG. 6, left), only those harboring NS5A or K3L were able to sustain growth under conditions of PKR expression (FIG. 6, right). Vector control transfectants exhibited a severe slow growth phenotype consistent with the growth suppressive activity associated with high levels of PKR expression (FIG. 6) (Romano et al., 1995). These results demonstrate that NS5A is sufficient to reverse PKR-mediated growth suppression in yeast, indicated that NS5A can directly repress PKR function. To confirm that PKR function was repressed in the presence of NS5A, we determined the level of eIF-2α phosphorylation in the RY1-1 transfectants. Similar to K3L, expression of NS5A resulted in approximately an 11-fold increase in the level of unphosphorylated eIF-2α over that observed in control transfectants harboring the vector alone (FIG. 7). While the majority of the eIF-2α in these cells remained in the hyperphosphorylated state, these results suggest that relatively small changes in the overall level of eIF-2α phosphorylation can nevertheless have dramatic effects on cell growth. Taken together, these observations indicate that NS5A, through a direct interaction with PKR, can repress PKR function in vitro resulting in alterations in the phosphorylation state of the PKR substrate, eIF-2α.

9. Example
MOLECULAR MECHANISM OF NS5A REPRESSION OF PKR FUNCTION

The following experiments were carried out to determine the mechanism of the NS5A-PKR interaction and the effects of ISDR mutations on NS5A regulation of PKR.

9.1. Materials and Methods

Plasmids pGBT10 and pGAD425 encode the GAL4 DNA binding domain (BD) and transcription activation domain (AD), respectively (Gale, Jr. et al., 1966 Mol. Cell. Biol. 16: 4172–4181). pAD-PKR K296R, pAD-PKR 244–5515, pAD-PKR 244–296 encode the indicated AD-PKR fusion constricts and have been described previously (Gale, Jr. et al., 1996). All NSSA-1b expression constructs were generated from pAD-NS5A which harbors wt NS5A from a clinical isolate of IFN-resistant HCV-1b (NSSA 1b-wt) (Gale et al., 1997, Virology 230:217–227). To facilitate yeast 2-hybrid protein interaction analysis, pAD-NS5A was cleaved with Ndel and BamHI restriction enzymes and the 1.4 kb insert encoding full-length NS5A (aa 1973–2419) cloned into the corresponding sites of pGBT10 to yield pBD-NS5A 1b-wt. PBD-NSSA 1973–2361 encodes a BD-fusion of NS5A aa 1973–2361 and was generated by subcloning the Ndel/Sal 1 insert from pBD-NS5A 1b-wt into the corresponding sites of pGBT10. pBC-NS5A 2120–2274 encodes a BD-fusion of NS5A aa 2120–2274 constructed by ligating the internal 462 bp EcoR1/BstY1 fragment from pBD-NS5A 1b-wt into the EcoR1/BamHI sites of pGBT10. pBD-NS5A 1973–2208, pBD-NS5A 2209–2274, and pBD-NS5A 2180–2251 encode BD-fusions of NS5A aa 1973–2208, 2209–2274 and 2180–2251, respectively and were generated by PCR amplification of the corresponding pBD-NS5A 1b-wt coding region using the restriction site linked oligonucleotide primer pairs shown in Table 3 (upper). PCR products were directly cloned into pCR2.1 (Invitrogen) as described by the plasmid manufacturer. PCR products encoding NS5A aa 1973–2208 and 2209–2274 were released from pCR2.1 by digestion with restriction enzyme combinations of Ndel/SalI or EcoRI/SalI, respectively. The resultant insert DNA was ligated into the respective sites of PGBT10 and pGBT9 (Clontech) to yield pBD-NS5A 1973–2208 and pBD2209–2274. The PCR product encoding NS5A aa 2180–2251 was released from pCR2.1 by Nco/BamHl digestion and the resultant 213 bp fragment was ligated into the identical sites of pAS2–1 (Clontech) to yield pBD-NS5A 2180–225 1. PBD-λISDR encodes and ISDR-deletion mutant of NS5A from IFN-resistant HCV-la (Gale et al., 1997, Virology 230:217–227).

Site-directed mutagenesis (Chameleon Double-Stranded Site-Directed Mutagenesis Kit; Strategene) was used to introduce ISDR mutations corresponding to IFN-sensitive strains of HCV-1b into pBD-NS5A 1b-wt. Mutagenesis reactions were carried out as described by the manufacturer using the mutagenic primers shown in Table 3 (lower). Template DNA was denatured by incubation at 100° C. for 5 minutes, followed by annealing of the indicated mutagenic primer and the Scal to StuI selection primer 5'GTGACTG-GTGAGGCCTCAACCAAGTC (StuI restriction site underlined). T7 DNA polymerase-primer extension products were ligated and selected for the primer-encoded mutations)

by digestion with ScaI restriction enzyme and subsequent transformation into XlmutS *E. coli* (Stratagene). By this method a set of isogenic NS5A constructs were constructed identical to NS5A 1b-wt except for the defined mutations introduced into the ISDR (see Table 1). pBD-NS5A 1b-2 and pBD-NS5A 1b-4 were generated directly from PBS-NS5A 1b-wt and encode a single (A2224V), or multiple (P2209L, T2214A, and T2217G) ISDR as mutations, respectively (Table 1). pBD-NS5A-5 encodes the ISDR mutations P2209L, T2214A, T2217G and A2224V, and was produced by introducing an A2224V mutation into pBD-NS5A-4.

For expression of NS5A in S. cerevisiae the entire 1.4 kb insert of pBD-NS5A 1b-wt was amplified by PCR using the restriction enzyme-linked oligonucleotides shown in Table 3 (upper). PCR products were cloned into the SrfI site of pCR-Script (Stratagene) and released from the resultant plasmid by HindIII digestion. The gel-purified insert DNA was cloned into the HindIII site of pYES2 (Invitrogen) to yield pYES-NS5A 1b-wt expressing NS5A under control of the galactose-inducible GAL1 promotor. Construction of pYES-NS5A 1b-2, PYES-NS5A 1b-4 and pYES-NS5A 1b-5 was facilitated by replacing the intemal 1.1 kb SacII/SalI fragment of pYES-NS5A 1b-wt with the internal SacII/SalI fragment from the respective pBD constructs.

For expression of NS5A in mammalian cells the entire 1.4 kb NS5A coding region of PYES-NS5A 1b-wt and pYES-NS5A 1b-5 was released by HindIII digestion and cloned into the HindIII site of pFLAG-CMV2 (Eastman Kodak Co.). The resulting plasmids, pFlagNS5A 1b-wt and pFlagNS5A 1b-5 respectively encode full-length wt and mutant NS5A fused at the N-terminus to the 8 aa FLAG epitope tag sequence (FLAG-NS5A) under control of the CMV immediate-early promotor. pNeo-NS5A 1a-wt was constructed by cloning the 1.4 kb HindIII/XbaI insert of pYES2-NS5A (Gale et al., 1997 Virology) into the corresponding sites of pcDNA1NEO. pNeo-PKR K296R encodes the full-length inactive human PKR K296R mutant (Barber et al., 1993 J. Biol. Chem. 170:17423–17428). For construction of pGST-NS5A 1b-wt the 1.4 kb NcoI/XhoI insert DNA from pAD-NS5A (Gale et al., 1997 Virology 230:217–227) was isolated and the 3' recessed termini filled in with Klenow polymerase (Sambrook et al., 1989 Molecular Cloning, 2nd edition, Cold Spring Harbor Press). The resulting blunt-ended DNA was cloned into the SmaI site of pGex-2TK (Pharmacia Biotech), fusing the NS5A coding region in-frame to the plasmid encoded GST protein. pGST-K3L encodes a GST fusion of the 88 aa vaccinia virus K3L protein. pGST-NS1 encodes a GST fusion of the influenza virus NS1 protein. The fusion between the N-terminal 132 aa of the phage λ cI repressor and the catalytically inactive PKR K296R was constructed in pcI168 to yield pcI-PKRK296R. The net sequence of each new construct was verified by dideoxynucleotide sequence analysis (Applied Biosystems).

Cell Culture and Transfection

NIH3T3, Cos-1 cells (ATCC) and tumor-derived cell lines were grown in Dulbecco's modified Eagle medium (DMEM) containing 10% fetal bovine serum as described (Tang et al., 1996 J. Biol. Chem 271: 28660–28666). For transient transfections, expression plasmid combinations were introduced into Cos-1 cells by the DEAE-dextran/chloroquine method exactly as described previously (Tang et al. 1996 J. Biol. Chem. 271-28660-28666) or by a procedure using the Superfect transfection reagent, as described by the manufacturer (Qiagen). Each set of transfections consisted of subconfluent 25 cm$^2$ cultures of approximately 6×10$^5$ cells co-transfected with 5 µg of each expression plasmid in the following combinations: pcDNA1neo/pNeoPKR K296R and pNeoNS5A1a-wt/pNeoPKR K296R, or pFlag/pNeoPKR K296R, pFlagNS5A1b-wt/pNeoPKR K296R or pFlagNS5A 1b-5/pNeoPKR K296R. Cells were harvested 48 hr post transfection and extracts processed for immunoprecipitation or immunoblot analyses as described. NIH3T3 cell lines stably expressing the PKR inhibitory protein $P_{58}^{IPK}$ have been described previously (Barber et al., 1994 Proc. Natl. Acad. Sci. 91:4278–4282). Vector control NIH3T3 cell lines or those expressing NS5A 1a-wt were derived by transfecting cells via the DEAE-dextran/chloroquine method with 3–10 µg of pcDNA1neo or pNeoNS5A 1a-wt respectively. Transfected cells were selected by growth in media containing 600 µg/ml of the neomycin analog G418. Drug-resistant clones were isolated, expanded and tested for stable expression of NS5A. By this method several clones were isolated expressing high or low levels of NS5A. Two representative clones were selected, 5C6 (high expressing) and 4A1 (low expressing) for further analyses.

PROTEIN ANALYSIS

Yeast extracts were prepared by collecting cells from 20 ml liquid cultures, washing once with ice cold water, resuspending in ice cold yeast lysis buffer [40 mM PIPES (pH 6.6), 100 mM NaCl, 1 mM DTT, 50 mM NaF, 37 mM β-glycerolphosphate, 120 mM AMSO$_{4,}$ 10 mM M2-aminopurine, 15 mM EDTA, 0.2 mM phenylmethylsulfonylflouride (PMSF)], and lysed by the glass bead method as described (Gale, Jr. et al., 1996 Mol. Cell. Biol. 16: 4172–4181). 3T3, Cos-1 and tumor-derived cell extracts were prepared in Bufferl [50 mM KCl, 50 mM NaCl, 1 mM EDTA, 1 mM DTT, 20% glycerol, 0.5% Triton X-100 units/ml aprotinin, 1 mM PMSF, 20 mM Tris (ph 7.5)] exactly as described (Tang et al., 1996 J. Biol. Chem. 271:28660–28666). Extracts were clarified by 4° C. centrifugation at 12,000×g, supernatants collected and stored at −70° C. Cell extract protein concentration was determined using the BioRad Bradford assay as described by the manufacturer (BioRad).

Determination of protein expression was carried out by immunoblot analyses of 25–50 µg total protein from cell extracts as previously described. Proteins were separated by SDS-PAGE and transferred to nitrocellulose membranes. Bound proteins were detected by probing the membranes with primary monoclonal antibodies specific to NS5A, (anti-NS5A) human PKR (anti-PKR (Laurent et al., 1985 Proc. Natl. Acad. Sci. 82:4341–4345) FLAG epitope (anti-FLAG; Eastman Kodak Co.), GAL4 activation domain or GAL4 DNA-binding domain [anti-AD and anti-BD, respectively (Clontech)]). Proteins were visualized by enhanced chemiluminscence (ECL) and autoradiography. To control for potential errors in protein loading, blots were also probed with actin-specific monoclonal antibody (anti-actin; ICN).

Immunoprecipitations were carried out from extracts representing 2×10$^6$ transfected Cos-1 cells. Extracts (150 µl) were thawed on ice and precleared by a 1 hr incubation with protein G-agarose beads (Boehringer Mannheim) at 4° C. Supenatants were recovered by 4° C. centrifugation (12, 000×g) and mixed with anti-NS5A (1:500) or antiFLAG M2-affinity gel (Eastman Kodak Co.) in a final volume of 600 µl buffer I and incubated at 4° C. for 2 hr or 16 hr, respectively. Anti-NS5A immunocomplexes were recovered by an additional incubation with protein G-agarose beads equilibrated in Buffer 1. Immunocomplexes were washed 5 times with 1 ml each of ice cold buffer 1. Anti-FLAG M2-affinity gel immunocomplexes were further washed 3 times with cold TBS [50 mM Tris (pH 7.5)] and eluted by the edition of competitor FLAG peptide as described by the manufacturer (Eastman Kodak Co.). Immunocomplexes were recovered by centrifugation, diluted in SDS-sample buffer and incubated at 100° C. for 5 min. Immunoprecipitation products were resolved by electrophoresis on 12% acrylamide/SDS gels and processed for immunoblot analysis as described above.

For isoelectric focusing of eIF-2α, yeast strains were grown 16 hr in uracil-deficient synthetic defined media containing 2% dextrose (SD), diluted to an $OD_{600}$ of 0.4 in uracil-deficient synthetic defined media containing 2% raffifiose and 10% galactose (SGAL), and grown for an additional 4–9 hr at 30° C. Yeast extracts were prepared as described for immunoblot analysis. Proteins (16 μg) were separated by vertical isoelectric focusing (Dever et al., 1993 Proc. Hatl. Acad. Sci. 90:4616–4620) and blotted to nitrocellulose membranes. eIF-2α was detected by immunoblot analysis using a rabbit polyclonal antisera specific to yeast eIF-2α. In these experiments, an increase in the level of the less acidic, basally-phosphorylated form of eIF-2α indicates a concomitant decrease in the level of hyperphosphorylated eIF-2α, which is phosphorylated by PKR on serine 51 (Dever et al., 1993 Proc. Natl. Acad. Sci. 90:4616–4620; Romano et al. 1995 Mol. Cell. Biol. 15:365–378). The levels of basally-phosphorylated eIF-2α relative to total were quantified by scanning laser densitometry and are presented as a percentage of total eIF-2α for each sample.

YEAST METHODS

Details of the yeast 2-hybrid assay have been extensively described (Gale, Jr. et al., 1996). This assay utilizes specific induction of His reporter gene to support growth of yeast strain Hf7c (Clontech) on histidine-deficient medium as an indicator of a 2-hybrid protein interaction. Saccharomyces cerevisiae strain Hf7c [MATa ura 3-52 his 3-200 lys2-801 ade2-101 trp 1-901 lea2-3, 112 gal-4–542 gal80-538 LYS2::GAL1-HIS3 URA3::(GAL4 17-mers)3-CYC1-lacZ] was transformed with the indicated 2μ Trp1 and Leu2 expression plasmids harboring the corresponding GALA AD- and BD-fusion constructs. Transformed strains were plated onto SD medium lacking tryptophan and leucine (+His). After 3 days at 30° C. strains were streaked onto SD medium lacking tryptophan, leucine and histidine (–His), and incubated for 3–6 days at 30° C. The resultant histidine-depleted colonies were replica-streaked onto +His and –His medium and incubated for 3–5 days at 30° C. Specific growth on –His medium was scored as positive for a 2-hybrid protein interaction.

For determination of PKR and NS5A function in vivo, wt or mutant NS5A Ura3 expression plasmids were transformed in S. Cerevisiae strain RY1-1 (MATa ura3-52 leu2-3 leu2-112 gcn 2Δ trp1-Δ63 LEU2::(GAL-CYC1-PKR)$_2$ (Romano et al., 1995). This strain lacks the yeast eIF-2α kinase GCN2, and harbors two copies of wt human PKR integrated into the LEU2 locus under control of the galactose inducible GAL/CYC1 hybrid promoter. When grown on SGAL medium PKR is expressed and phosphorylates endogenous eIF-2α on serine 51, resulting in inhibition of mRNA translation and growth suppression (Dever et al., 1993; Romano et al, 1995). Conversely, coexpression of wt NS5A represses these toxic effects associated with PKR function in this system, allowing strains coexpressing functional NS5A to grow on SGAL medium (Gale et al., 1997). RY1-1 strains harboring the indicated NS5A expression constructs were plated onto non-inducing uracil-deficient SD medium and incubated at 30° C. for 3 days. Single colonies were picked and cultured for 16 hr at 30° C. in uracil-deficient liquid SD media. Aliquots of each culture were normalized to an $OD_{600}$ of 0.2 and serially diluted in 10-fold increments with sterile $H_2O$. 2 μl of each dilution were applied in replicate onto uracil-deficient SD and SGAL medium, and incubated for 3–6 days at 30° C. Strains were scored for high dilution growth on SGAL medium which is indicative of NS5A-mediated repression of PKR (Gale et al., 1997).

Dimerization Disruption Assay

The assay to measure PKR dimerization disruption has been previously described (Hu, 1990 Science 250: 1400–1403; Hu, 1995 Structure 3:431–433) This assay utilizes sensitivity to phage λ-mediated cell lysis as an indicator of the dimerization state of cI-PKR K296R fusion protein expressed from pcI-PKR K296R in E. coli. pcI-PKR K296R replicated under control of the p15A ori and is thus a low-copy replicon compatible with plasmids that contain the colEi ori, including the pGEX series of vectors (Smith et al. 1988, Gene 67, 31–40). E. Coli strain AG1688 (Hu, 1990) co-expressing cl-PKR K296R and the indicated GST-fusion protein was assessed for resistance to cell lysis mediated by the phage λ cI-deletion mutant λKH54 (Hu, 1990). AG1688 E. coli. were grown to midlog phase in liquid cultures consisting of Luria broth supplemented with 10 mM $MgSO_4$ and 0.2% maltose. Bacteria (2.5 μl aliquots) were mixed with an equal volume of serial 10-fold dilutions of λKH54 containing $10^2$–$10^6$ plague forming units each. The bacteria-phage mixture was applied to antibioticagar plague forming units each. The bacteria-phage mixture was applied to antibiotic-agar plates containing 0.1 mM isopropylthio-B-D galactoside (IPTG) to induce expression of the plasmid-encoded fusion proteins. Plates were air dried, incubated 16 hr at 37° C., and scored for resistance to λKH54-mediated cell lysis which is an indicator for in vivo formation of funcational cI-PKR K296R homodimers. The expression of each plasmid-encoded fusion protein was verified by immunoblot analysis.

Cell Growth Analysis and Tumorgenicity Assays

Growth characteristics of stable NIH3T3 cell lines constitutively expressing transfected NS5A or $P_{58}^{IPK}$ (control) (Barber et al., 1994) were determined as described in Table 2. For analysis of tumor phenotypes, tumors were excised from nu/nu mice under sterile conditions, washed in phosphate buffered saline (PBS) and minced into 1–5 mm fragments. Tumor fragments were homogenized by first incubating in 1% collagenase/0.1% Dispase (Gibco BRL) in PBS and then blending in a Dounce vessel homogenizer. Homogenized tumors were incubated at 37° C. for 2 hr., centrifuged at 600×g for 10 min and resuspended in fresh DMEM with 10% FCS. Cell suspensions were seeded into multi-well plates for the generation of clonal tumor-derivee cell lines.

8.2 Results

Mechanism of PKR Regulation by NS5A: Disruption of Potein Kinase Dimerization

Viral-control of PKR occurs at multiple levels, defining specific steps within the PKR maturation, activation and catalytic processes. These steps include, but are not limited to, modulation of PKR levels, regulation of dsRNA-binding events, protein kinase dimerization, and regulation of PKR catalytic activity. As described herein by the Applicants, NS5A binding to PKR was mapped to within a broad region of the PKR catalytic domain defined by PKR aa 244–355. To begin to understand NS5A-mediated regulation of PKR, the molecular mechanisms of NS5A-binding domain on the protein kinase was investigated. In order to identify the NS5A-binding domain on the protein kinase, protein interaction analysis were carried out using wild type (wt) NS5A from an IFN-resistant isolate of HCV-1b (1b-wt; see Table 1) fused to the GAL4 DNA binding domain (BD-NS5A 1b-wt). The ability of this construct to mediate interaction with PKR deletion mutants fused to the GAL4 transcription activation domain (AD) in a yeast 2-hybrid assay was tested. A 2-hybrid protein interaction was determined by the ability of co-transformed yeast to grow on histidine-def icient (−His) medium which is due to activation of the Hf7c His reporter. It was determined that each construct was efficiently expressed in the corresponding strains. As seen in FIG. 8 Hf7c yeast strains co-expressing BD-NS5A 1b-wt with AD-PKR (PKR K296R) or the AD-PKR deletion constructs, PKR 244–551 or PKR 244–296, all exhibited growth on −His medium, demonstrating a 2-hybrid protein interaction within these strains. Thus, it was determined that the NS5A the 52 aa sequence defined by PKR aa 244–296 was sufficient to mediate interaction with NS5A. These results define the NS5A binding domain of PKR to within aa 244–296, which as described herein is a critical PKR dimerization domain.

The ability of NS5A 1b-wt to interfere with PKR dimerization in vivo was tested using a phage λ-based genetic assay in $E.\ coli$. In this assay, dimerization proteins, which are fused in frame to the DNA-binding domain of the phage λ CI repressor, mediate dimerization of the CI DNA-binding domain, which is required for binding to the λ promotor (Hu, 1995 Structure 3:431–433). When expressed in $E.\ coli$, the hybrid CI repressor mediates resistance to cell lysis induced by a CI-deletion mutant of λ phage [λKH54; (Hu, 1990 Science 250:1400–1403)] by dimerizing and binding to the λ promoter. This results in repression of phage gene expression within λKH52-infected $E.\ coil$ that express the hybrid CI-repressor. Conversely, co-expression of a dimerization inhibitor in this system releases λ gene repression through the disruption of CI dimers, resulting in $E.\ coli$ lysis. Expression of full length inactive PKR K296R fused at the N-terminus to the CI DNA-binding domain (CI-PKR) is sufficient to repress λ gene expression upon λKH54 infection in $E.\ coli$. This is demonstrated in FIG. 9 where co-expression of GST had no effect on CI-PKR-mediated λ gene repression, as resistance to cell lysis was observed even after exposure to high concentrations of phage (FIG. 9, lane 1). Thus the PKR component of CI-PKR facilitates protein dimerization and λ gene repression in vivo. Resistance to λKH54-mediated cell lysis was reduced approximately 1000-fold in $E.\ coli$ co-expressing CI-PKR with GST-NS5A (compare lanes 1 and 2, FIG. 9), indicating that NS5A was disrupting the CI-PKR dimerization process. This effect of GST-NS5A 1b-wt was shown to be specific to CI-PKR. Thus, NS5A specifically disrupts the PKR dimerization process in vivo.

Further, NS5A-mediated disruption of PKR dimerization is consistent with the region targeted by NS5A for binding to PKR which localizes to a PKR dimerization domain (see FIG. 8). Indeed, GST constructs encoding other viral inhibitors of PKR, including vaccinia virus K3L (GST-K3L; lane 3) and influenza virus NS1 (GST-NS1; lane 4), which respectively target the PKR-substrate (Craig et al., 1996 J. Biol. Chem. 271–24526–24533; Gale, Jr. et al., 1996 Mol. Cell. Biol. 16:4172–4181) and -dsRNA interactions (Katze et al., 1991), did not affect the ability of $E.\ coli$ to resist λKH54-mediated cell lysis when co-expressed with CI-PKR. Thus, NS5A represents a new class of PXR inhibitors which repress PKR function by disrupting PKR dimerization thus defining the dimerization step as a critical component in the processes of PKR maturation, activation and catalytic function and a key target for screening assays to identify novel antivival agents.

9. Example
NS5A, PKR Regulation, and IFN Sensitivity: Redefining the ISDR

Recent molecular epidemiological studies have identified the ISDR as a conserved region with the HCV genome of IFN-resistant strains of HCV-1b. Applicants have determined that NS5A from IFN-resistant strains of HCV genotypes 1a and 1b can bind to PKR to repress kinase function in vivo, a process dependent upon the NS5A ISDR. Using a series of NS5A ISDR variants isogenic to NS5A 1b-wt. Applicants have demonstrated that mutations within the ISDR can abrogate the PKR-regulatory properties of NS5A in vivo.

9.1 Identification of the PKR-Interacting Domain of NS5A: the ISDR is Necessary but not Sufficient for NS5A-PKR Complex Formation A detailed structural analysis of the NS5A-PKR interaction was conducted using the yeast-2-hybrid assay to determine the role of the ISDR in this interaction. TRP1 plasmids encoding full-length or deletion mutants of BD-NS5A 1b-wt (FIG. 10A; see Table 1), were introduced into yeast strain Hf7c harboring a LEU2 plasmid encoding AD-PKR. All constructs were efficiently expressed in co-transformed strains (FIG. 10C). Strains harboring each BD-NS5A construct and AD-PKR or AD-vector (interaction-negative control) all grew on medium containing histidine. Interaction-negative control strains failed to grow on −His medium, demonstrating specificity for the described interactions. Importantly, it was found that an ISDR-inclusive 66 aa region of NS5A was required for complex formation with PKR in vivo (FIG. 10). The NS5A N-terminal 236 aa alone were not sufficient to interact with AD-PKR as determined by the inability of strains harboring this construct to grow on −His medium (FIG. 10B). Moreover, it was found that the ISDR-inclusive construct encoding NS5A aa 2180–2251 did not support growth on −His medium when expressed with AD-PKR. Conversely, those strains harboring BD-NS5A constructs 1973–2419, 1973–2361, or 2120–2274 exhibited growth on −His medium, implying a 2-hybrid protein interaction. By these analyses it was determined that the PKR-binding region of NS5A maps to within a 66 aa region comprising the ISDR and the adjacent C-terminal 26 aa (FIG. 10B, lower). Thus, the ISDR was necessary but not sufficient for the NS5A-PKR interaction.

9.2 THE NS5A-PKR Interaction is Dependent Upon the Sequence of the ISDR

The yeast 2-hybrid assay was used to examine the effects, if any, that defined the ISDR mutations had on in vivo complex formation between NS5A and PKR. A series of NS5A expression plasmids encoding wild type (wt) and ISDR variants of NS5A corresponding to IFN-resistant and -sensitive strains of HCV, respectively. Rather than randomly assigning ISDR mutations, site-directed mutagenesis was used to construct ISDR variants of NS5A based upon defined mutations previously identified within clinical isolates of IFN-sensitive strains of HCV (Enomoto et al., 1996 N. Eng J. Med. 334:77–81). These mutations, shown in Table 1, were introduced into the ISDR of NS5A 1b-wt, previously isolated from IFN-resistant HCV (Gale et al., 1997). A set of isogenic NS5A constructs, 1b-2, 1b-4 and 1b-5 was generated which respectively contained two, four and five aa changes from the prototype ISDR sequence from IFN-resistant HCV. These constructs are identical in sequence to NS5A 1b-wt except for defined mutations within the ISDR, thus allowing a determination of the effect of specific ISDR mutations on HCV-1b NS5A function. Table 1 compares the ISDR sequence and IFN-response of the prototype IFN-resistant HCV-J strain (Kato et al., 1990 Proc. Natl. Acad. Sci. USA 87:9524–9528) with the ISDR sequence and response to IFN determined for the corresponding viral isolate from each wt and mutant NS5A construct.

BD-NS5A constructs encoding full-length 1b-wt NS5A and isogenic ISDR variants (Table 1) were transformed into Hf7c yeast harboring plasmid-encoded AD-PKR or the AD control vector. As additional controls, a parallel assessment of strains harboring plasmids encoding AD-PKR and the HCV-1a NS5A constructs BD-1a-wt (positive control) or BD-ΔISDR (negative control) were included, the latter lacking the complete ISDR of the corresponding 1a-wt construct (Gale et al., 1997). The resulting yeast strains were replica printed onto +His and –His medium. As shown in FIG. 11 all strains grew on +His medium. However, only those strains expressing BD-NS5A constructs 1b-wt, 1b-2 or the 1a-wt control exhibited growth on –His medium, indicating that these constructs could bind PKR in vivo. Similar to the ΔISDR control, ISDR variants of BD-NS5A, 1b-4 and 1b-5 failed to interact with AD-PKR, as strains containing these constructs failed to grow on –His medium (FIG. 11A). Immunoblot analyses demonstrated that all BD-NS5A constructs and the AD-PKR construct were efficiently expressed in co-transformed yeast (FIG. 11B). Thus, isogenic NS5A constructs differing in their ISDR sequence differentially interacted with PKR in vivo. Introduction of a single ISDR point mutation (NS5A 1b-2) was not sufficient to abolish the NS5A-PKR interaction. while conversely, multiple ISDR mutations did abolished complex formation with PKR (FIG. 11A). The inability of NS5A to bind PKR can therefore be attributed to multiple mutations within the ISDR which, importantly, have been associated with IFN-sensitive HCV.

9.3 ISDR Mutations Abolish NS5A Function

NS5A represses PKR function through a direct interaction with the protein kinase (Gale et al., 1997b). Multiple ISDR mutations disrupt NS5A-PKR complex formation (FIG. 11). Therefore, the ability of wt and ISDR variants of NS5A to regulate PKR function was compared in vivo. Expression plasmids encoding NS5A constructs 1b-wt, 1b-2, 1b-4 and 1b-5 under control of the Gal promotor, were introduced into the gcn2ΔS.cerevisiae strain RY1-1 (Romano et al., 1995 Mol. Cell. Biol. 15:365–378). This strain lacks the endogenous GCN2 protein kinase and harbors two integrated copies of wt human PKR under control of a galactose-inducible GAL/CYC hybrid promotor. When placed on galactose medium, PKR is expressed and phosphorylates serine 51 on eIF-2α resulting in suppression of cell growth (Romano et al., 1995 Mol. Cell. Biol. 15:365–378). As seen in FIG. 12A, strains harboring the respective NS5A expression plasmid or the expression plasmid alone (vector; control) grew equally well when cell equivalents were serially plated onto non-inducing medium containing dextrose as the sole carbon source (left panel). In contrast, only the strain co-expressing NS5A 1b-wt exhibited significant growth on inducing medium (FIG. 12A, right panel). By this method it was determined that strains co-expressing NS5A 1b-wt with PKR exhibited greater than a 100-fold increase in plating efficiency when grown on galactose medium compared to those strains co-expressing NS5A 1b-4 or 1b-5 and PKR. It was also observed a reduced plating efficiency, corresponding to a 10–100-fold decrease, in strains co-expressing PKR and NS5A 1b-2 (FIG. 12A). This was surprising since this construct was able to bind to PKR in our yeast 2-hybrid assay (see FIG. 11). These results demonstrate that introduction of a single aa point mutation (A252V) within the ISDR of 1B-wt was sufficient to uncouple repression of PKR from NS5A-PKR complex formation. Multiple ISDR aa mutations, corresponding to IFN-sensitive strains of HCV, resulted in loss of the growth-restoration phenotype associated with isogenic NSSA 1b-wt. These results indicate that NS5A 1b-wt repressed the translational regulatory properties of PKR in vivo, resulting in restoration of cell growth and stimulation of protein synthesis. The loss of function associated with the NS5A ISDR variants suggest that the PKR-regulatory properties of NS5A were disrupted by the introduction of mutations within the ISDR.

To determine the effect of ISDR mutations on the PKR-regulatory function of NS5A analysis of the endogenous in vivo phosphorylation state of the PKR substrate, eIF-2α was conducted. Repression of PKR function in RY1-1 yeast strains results in a reduction in the level of the hyper-phosphorylated form of eIF-2α, phosphorylated exclusively by PKR on serine 51 (Romano et al., 1995 Mol. Cell. Biol. 15:365–378). Using single-dimensional isoelectric focusing (IEF) the hyper-phosphorylated form of eIF-2α can be electrophoretically separated from the less acidic, hypo-phosphorylated form, which lacks serine 51 phosphorylation (Dever et al., 1993). FIG. 10 shows an immunoblot from an IEF gel of extracts prepared from the RY1-1 strains represented in FIG. 12 which was probed with antisera specific to yeast eIF-2α. As controls, extracts from strains harboring the expression plasmid, devoid of insert (V, lane 1), or the transdominant-negative PKR mutant, PKR Δ295–300 (FIG. 12, lane 6) were included. PKR Δ295–300 inhibits wt PKR when co-expressed in yeast, resulting in reduced levels of serine 51 phosphorylation and restoration of cell growth when plated on galactose medium (Romano et al., 1995). As seen in FIG. 13 strains expressing NS5A 1b-wt or PKR Δ295–300 exhibited a significant reduction in the level of hyper-phosphorylated eIF-2α, as demonstrated by a concomitant increase in the abundance of the hypo-phosphorylated eIF-2α isoform relative to the vector control strain (compare lanes 1 and 2). Strains expressing the isogenic NS5A variants, 1b-2, 1b-4 or 1b-5 possessed predominantly the hyper-phosphorylated isoform of eIF-2α, similar to the vector control strain (FIG. 13, compare lanes 3–5 with lane 1). The respective level of serine 51-phosphorylated eIF-2α corresponded with the growth phenotype of each strain on galactose medium (FIG. 12A), where expression of NS5A 1b-wt facilitated growth on galactose and a reduction in serine 51-phosphorylation. This phenotype was reversed by the introduction of ISDR mutations into NS5A. These results, taken together, demonstrate that ISDR mutations which correspond to IFN-sensitive HCV (Table 1) can disrupt the PKR-regulatory properties of NS5A. Moreover, the uncoupling of PKR-binding events from NS5A-directed PKR inhibition observed in our analyses of the NS5A 1b-2 construct (see FIGS. 11 and 12) indicates that abrogation of NS5A function can occur at multiple levels and is not limited to disruption of NS5A-PKR complex formation.

9.4 THE NS5A-PKR Interaction in Mammalian CElls is Disrupted by ISDR Mutations NS5A from IFN-resistant HCV represses the translational regulatory properties of PKR when expressed in mammalian cells (Gale et al., 1997). As suggested by the results from the yeast 2-hybrid (FIG. 11) and growth assays (FIG. 12), Applicants hypothesized that the NS5A-directed repression of PKR occurring in mammalian cells was similarly mediated through a direct NS5A-PKR interaction. Applicants sought to determine if NS5A and PKR could form a stable complex in mammalian cells and what effect, if any, ISDR mutations had on complex formation. Co-immunoprecipitation analyses from Cos-1 cells transiently co-transfected with plasmids encoding wt or ISDR variants of NS5A and full length inactive human PKR. In these analyses, plasmids were utilized encoding NS5A from IFN-resistant HCV-1a (1a-wt), 1b-wt and the 1b isogenic variant, 1b-5; the latter corresponding to IFN-sensitive HCV (Table 1). Immunoblot analysis of extracts prepared from co-transfected cells demonstrated that all constructs were efficiently expressed within 48 hr of transfection (FIG. 14). PKR was recovered from anti-NS5A immunoprecipitates prepared from cells cotransfected with 1a-wt, and from anti-FLAG immunoprecipitates prepared from cells harboring FLAG-tagged 1b-wt (FIG. 14A and B, respectively). In comparison, no PKR was detected in immunoprecipates of Flag-tagged 1b-5 (compare lanes 5 and 6; FIG. 14). Recovery of PKR was dependent upon the presence of NS5A in the extract, as we failed to detect PKR in NS5A-specific immunoprecipitates prepared from extracts lacking wt NS5A (FIG. 10A and 10B, lanes 1 and 4, respectively). These results demonstrate that NS5A from IFN-resistant strains of HCV-1a and HCV-1b can form a stable and specific complex with PKR when expressed in mammalian cells. Similar to the yeast 2-hybrid results (FIG. 11, mutations within the ISDR which correspond to IFN-sensitive HCV (Table 1) disrupted the NS5A-PKR interaction within mammalian cells. The consistency between these results and those observed within the yeast studies (see FIGS. 11 and 12) validates the yeast system as viable model for the study of NS5A-PKR interaction and the effects of this interaction on PKR function.

10. Example: NS5A Possesses Oncogenic Potential

Since the PKR regulatory pathway has been linked to the control of cell growth, Applicants addressed the question of whether PKR regulation by NS5A may play a role in the development of a malignancy with chronic HCV infection. In this study, it was proposed that oncogenic transformation was occurring through repression of PKR-dependent eIF-2α phosphorylation and deregulated mRNA translation. NS5A from IFN-resistant HCV binds to PKR (FIG. 14) and represses the translational-regulatory properties of PKR in mammalian cells. Results from the yeast systems indicate that NS5A possesses growth-stimulatory properties through the repression of PKR-mediated eIF-2α phosphorylation (see FIGS. 12 and 13). To determine if NS5A repression of PKR similarly conferred growth-stimulation to mammalian cells, NIH-3T3 cells constitutively expressing NS5A 1a-wt from the CMV immediate-early promotor were established. Two such cell lines, NS5A 5C6 and NS5A 4A1, were chosen for study. Immunoblot analysis revealed that NS5A 5C6 expressed high levels of NS5A (FIG. 15) while NS5A 4A1 cells expressed NS5A at significantly lower (data not shown). The growth properties of these cell lines were examined including the ability to form tumors when injected into athymic nu/nu mice (Table 2). As controls in the analyses, the following control cell lines were included: an NIH-3T3 cell line similarly derived with the empty transfection plasmid (neo 5–10), or a previously described cell line, P58-20 which overexpresses the PKR inhibitory protein $p_{58}^{IPK}$ (Barber et al., 1994). Similar to the P58-20 cell line, NS5A 5C6 cells exhibited approximately a 40% reduction in doubling time and with a 2.5–3 fold increase in culture saturation density when compared to the neo 5–10 control (Table 2). The growth rate of the NS5A low-expressing cells, NS5A 4A1, did not significantly differ from the neo 5–10 controls. However, these cells did exhibit a reproducible two-fold increase in culture saturation density when compared to control cultures (Table 2). Thus, constitutive expression of NS5A in NIH-3T3 cells supported cell division in post-confluent cultures and was associated with an increased rate of cell growth. These results were consistent with the Ephenotype of the malignantly transformed P58-20 control cells (Barber et al., 1994).

To further characterize the phenotype of the NS5A cell lines, the ability of these cells to undergo anchorage-independent growth in vitro and to form tumors in athymic mice was evaluated. Similar to the P58-20 control, NS5A 5C6 cells formed colonies when cultured on soft-agar medium, with an apparent 14-fold increase in cloning efficiency when compared to neo 5–10 cells. Anchorage-independent growth was similarly observed for NS5A 4A1 cells albeit at a significant lower frequency (Table 2). Importantly, both NS5A cells lines generated tumors after injection into athymic mice. NS5A 5C6 cells aggressively formed tumors in 5/5 mice with a latency period ranging from 17–25 days post-injection of cells. We observed a significantly longer latency period for tumor formation (22–44 days) in with mice which received NS5A 4A1 cells. Those mice receiving control P58-20 cells exhibited aggressive tumor growth with a latency period ranging from 12– 20 days, similar to previous results (Barber et al., 1994). NS5A expression was confirmed in tumor-derived cells prepared from those tumors recovered from NS5A 5C6 (FIG. 15) and 4A1 mice. Moreover, a preliminary examination of these cells revealed that endogenous eIF-2α phosphorylation was significantly reduced, consistent with NS5A-mediated repression of PKR. This study demonstrates that constitutive expression of NS5A, corresponding to IFN-resistant HCV-1a, can induce cell growth-deregulation and malignant transformation in NIH-3T3 cells.

The results indicate that NS5A-directed repression of PKR not only has implications for how HCV responds to IFN therapy, but also suggests that this process may contribute to the development of malignancy associated with chronic HCV infection. Thus, these findings demonstrate that screening assays to identify antiviral agents which inhibit NS5A disruption of PKR dimerization, may also identify agents which inhibit the development of malignancies associated with chronic HCV infection.

A number of references have been cited and the entire disclosures of which are incorporated herein by reference.

The present invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

TABLE 1

ISDR sequence and corresponding IFN sensitivity of isogenic NS5A expression constructs.

| Name[a] | ISDR Sequence (aa 2209–2248) | IFN Response[b] | Reference |
|---|---|---|---|
| 1b-pt | PSLKATCTTHHDSPDADLIEANLLWRQEMGGNITRVESEN | R | (Enomoto et al., 1996) |
| 1b-wt | ---------R-------------------------- | R | (Clements and Zink, 1996) |
| 1b-2 | ---------R-----V-------------------- | R/S | (Enomoto et al., 1996; Zeuzem et al., 1997) |
| 1b-4 | L----A--GR-------------------------- | S | |
| 1b-5 | L----A--GR-----V-------------------- | S | (Enomoto et al., 1996) |
| 1a-wt | --------AN------E------------------- | S | (Gale et al., 1997b) |

[a]pt, HCV-J prototype reference sequence (GenBank™ accession no. D90208); we, wild type parental HCV-1b clone [GenBank™ accession no. AF034151 (NS5A coding region only)].
[b]R, IFN resistant; S, IFN sensitive; R/S, independently reported as IFN-sensitive in separate studies. The IFN-response phenotype corresponding to 1b-4 has not been determined. However, based upon published studies (Enomoto et al., 1996; Kurosaki et al., 1997) we predict this sequence to be associated with sensitivity to IFN.

TABLE 2

Growth properties of cells expressing NS5A.

| Clone[a] | Doubling time (hrs)[b] | Saturation density (cells × $10^3$/cm$^2$)[b] | Cloning efficiency (%)[c] | Mice with tumors/total[d] | Latency (days)[d] |
|---|---|---|---|---|---|
| neo5-10 | 27.6 ± 0.1 | 1.6 ± 0.1 | 0 | 0/5 | — |
| NS5A 5C6 | 17.7 ± 0.6 | 4.0 ± 0.2 | 14 | 5/5 | 17–25 |
| NS5A 4A1 | 22.4 ± 2.1 | 3.3 ± 0.1 | 4 | 4/5 | 22–44 |
| P58-20 | 17.3 ± 1.5 | 3.7 ± 0.2 | 15 | 5/5 | 12–20 |

[a]neo5-10 and P58-20 represent − and + control cell lines, respectively. NS5A 5C6 cells express NS5A to levels approximately 5-fold higher than NS5A 4A1 cells.
[b]cells were seeded at $10^5$ cells/55 mm culture dish in selective DMEM containing 10% fetal bovine serum (FBS) and 400 μg/ml G418. Cells were counted every 24 hr and saturation density determined by measuring the number of total cells in culture 4 days after reaching confluency. Numbers show an average of 4 experiments.
[c]$5 \times 10^2$, $4 \times 10^3$ or $10^4$ ce;;s were suspended in 0.35% agar/DMEM solution with 20% FBS, and overlaid in duplicate onto 6-well culture dishes containing 0.7% agar/DMEM with 10% FBS. Cloning efficiency was determined 14 days later and is presented as a percentage of the number of colonies observed/total number of cells plated. Colonies were defined as an isolated cluster of 4 or more cells.
[d]4–6 week old athymic nude mice [nu/nu (Charles River)] were injected subcutaneously near the left hind limb with $2 \times 10^6$ cells in PBS. Mice were housed in microisolator cages in a pathogenfree facility and observed for up to 100 days. Latency was defined as the time, in days, to produce 3 mm diameter tumors.

TABLE 2

Growth properties of cells expressing NS5A.

| Construct[a] | Sense[b] | Antisense | nt |
|---|---|---|---|
| NS5A 1b-wt 1973–2419 | 5'TA<u>AGCTT</u>ATGGGCT CCGGCTCGTGGCT | 5'CA<u>AGCTT</u>GGATCCT TAGGACATTGAGC | 6260–7598 |
| NS5A 1973–2208 | 5'<u>CATATG</u>GGCTCCGG CTCGTGGCTA | 5'<u>GTCGAC</u>CGCAGACA ACTGGCTAGCTGA | 6260–6965 |
| NS5A 2209–2274 | 5'<u>GAATTC</u>CCTTCCTT GAAGGCAACATGC | 5'ATC<u>GGATCC</u>TTATA CCACCTTATTCTCTGA | 6966–7165 |
| NS5A 2180–2251 | 5'CCTT<u>CCATGG</u>CCCA CATTACAGCAGAGACG | 5'ATC<u>GGATCC</u>TTATA CCACCTTATTCTCTGA | 6877–7094 |

| Construct | Mutagenic Primer | Mutation |
|---|---|---|
| NS5A 1b-2 NS5A 1b-5 | 5'GACTCCCCAGAT<u>GTT</u>GACCTCATC | A2224V |
| NS5A 1b-4 | 5'TTGTCTGCG<u>CTT</u>TCCTTGAAGGCAGCAT<u>GC</u>ACT <u>GGC</u>CGTCACGAC | P2209L, T2214A, T2217G |

[a] aa and nt positions correspond to the PCR-amplified region. Numbering is based on the prototypic HCV-J sequence (Kato et al., 1990).
[b] Underlined sequence denotes cloning restriction site (described in text).
[c] Underlined condons correspond to the indicated aa mutations.

---

What is claimed is:

1. A method for screening for a potential novel agent effective to inhibit the development of malignancies associated with a chronic viral infection, whereby said viral infection is caused by a virus which contains a viral protein with an interferon sensitivity determining region (ISDR), comprising:

incubating a PKR protein kinase, the viral protein, and one or more agents to be tested, and measuring PKR protein kinase activity, comparing to PKR protein kinase activity with a control in the absence of the agent to be tested, and identifying a potential agent by the indication of PKR protein kinase activity in the presence of a test agent.

2. The method of claim 1 wherein the agent inhibits the malignancies associated with chronic hepatitis C viral infection.

3. The method of claim 1 wherein the viral protein is NS5A.

4. A method for screening for a potential agent effective to inhibit the development of malignancies associated with a chronic viral infection, whereby said viral infection is caused by a virus which contains a viral protein with an interferon sensitivity determining region (ISDR), whereby said agent is effective in inhibiting the direct interaction of an ISDR containing viral protein with an interferon induced PKR kinase, comprising:

incubating the ISDR containing protein, a PKR protein kinase and one or more agents to be tested, and measuring the binding of the ISDR containing protein and the PKR protein, comparing to the degree of binding with a control in the absence of the agent to be tested, and identifying a potential agent by the indication of PKR protein kinase activity in the presence of a test agent.

5. The method of claim 4 wherein the viral protein is NS5A.

6. The method of claim 4 wherein the agent inhibits the malignancies associated with chronic hepatitis C viral infection.

7. The method of claim 1, wherein the PKR protein kinase and the protein containing an ISDR are expressed in a yeast cell genetically engineered to increase expression of a reporter gene in the presence of activated PKR protein kinase, and further comprising measuring the level of expression of the reporter gene in the presence and absence of the agent to be tested.

8. The method of claim 7, wherein the reporter gene product is fused to GCN4/β-gal protein.

9. A method for screening for agents that alter the activation of an interferon-induced PKR protein kinase, the method comprising:
   (a) contacting an agent with a yeast cell which is genetically engineered to express:
      (i) a polypeptide containing an ISDR region, and
      (ii) an interferon-induced PKR protein kinase, and
      (iii) a reporter gene whose expression is increased in response to activation of the PKR protein kinase;
   (b) measuring the level of expression of the reporter gene in the presence of said agent;
   (c) comparing the level of expression of the reporter gene in the presence of said agent to the level of expression in the absence of said agent, wherein a difference indicates that said agent alters the activity of an interferon-induced PKR protein kinase.

10. The method of claim 9 wherein the polypeptide containing an ISDR region is NS5A.

11. The method of claim 10 wherein the reporter gene is a fused GCN4/β-gal gene.

12. A method for screening for a potential novel antiviral agent effective to inhibit the activity of a viral protein containing an interferon sensitivity determining region (ISDR), comprising:
   incubating a PKR protein kinase, the viral protein, and one or more agents to be tested, and
   measuring PKR protein kinase activity,
   comparing to PKR protein kinase activity with a control in the absence of the agent to be tested, and identifying a potential antiviral agent by the indication of PKR protein kinase activity in the presence of a test agent.

13. The method of claim 12 in which the antiviral agent inhibits hepatitis C viral replication.

14. The method of claim 12 wherein the viral protein is NS5A.

15. The method of claim 12, wherein the PKR protein kinase and the protein containing an ISDR are expressed in a yeast cell genetically engineered to increase expression of a reporter gene in the presence of activated PKR protein kinase, and further comprising measuring the level of expression of the reporter gene in the presence and absence of the agent to be tested.

16. The method of claim 15, wherein the reporter gene product is fused to GCN4/β-gal protein.

17. A method for screening for a potential antiviral agent effective in inhibiting the direct interaction of an ISDR containing viral protein with an interferon induced PKR protein kinase, comprising:
   incubating the ISDR containing protein, a PKR protein kinase and one or more agents to be tested, and
   measuring the binding of the ISDR containing protein and the PKR protein,
   comparing to the degree of binding with a control in the absence of the agent to be tested, and identifying a potential antiviral agent by the indication of PKR protein kinase activity in the presence of a test agent.

18. The method of claim 17 wherein the viral protein is NS5A.

19. The method of claim 17 in which the antiviral agent inhibits hepatitis C viral replication.

20. A yeast cell for use in a screen for antiviral agents, which is genetically engineered to express:
   (a) a polypeptide containing an ISDR region, and
   (b) an interferon-induced PKR protein kinase, and
   (c) a reporter gene whose expression is increased in response to activation of the PKR protein kinase.

21. The yeast cell of claim 20 wherein the polypeptide containing an ISDR region is NS5A.

22. The yeast cell of claim 21 wherein the reporter gene is a fused GCN4/β-gal gene.

* * * * *

UNITED STATES PATENT AND TRADEMARK OFFICE
CERTIFICATE OF CORRECTION

PATENT NO.    : 6,326,151 B1                                              Page 1 of 1
DATED         : December 4, 2001
INVENTOR(S)   : Michael G. Katze and Michael J. Gale, Jr.

It is certified that error appears in the above-identified patent and that said Letters Patent is hereby corrected as shown below:

Column 1,
Line 9, after "Mar. 5, 1997." add -- This invention was made with United States Government support under Grant Numbers AI22646 and RR00166 awarded by the National Institutes of Health. The United States Government has certain rights in the invention. --

Signed and Sealed this

Twentieth Day of August, 2002

Attest:

Attesting Officer

JAMES E. ROGAN
Director of the United States Patent and Trademark Office